US007820418B2

(12) United States Patent
Karl et al.

(10) Patent No.: US 7,820,418 B2
(45) Date of Patent: Oct. 26, 2010

(54) CORN FRACTIONATION METHOD

(75) Inventors: Daniel W. Karl, St. Paul, MN (US);
Charles R. Anderson, Apple Valley, MN (US); Alexa Hart, St. Paul, MN (US); Jeremy Owen, St. Louis Park, MN (US)

(73) Assignee: GrainValue, LLC, West St. Paul, MN (US)

( * ) Notice: Subject to any disclaimer, the term of this patent is extended or adjusted under 35 U.S.C. 154(b) by 609 days.

(21) Appl. No.: 11/629,810

(22) PCT Filed: Jun. 27, 2005

(86) PCT No.: PCT/US2005/022919
§ 371 (c)(1),
(2), (4) Date: Apr. 19, 2007

(87) PCT Pub. No.: WO2006/004748
PCT Pub. Date: Jan. 12, 2006

(65) Prior Publication Data
US 2007/0184541 A1 Aug. 9, 2007

Related U.S. Application Data

(63) Continuation-in-part of application No. 10/877,451, filed on Jun. 25, 2004.

(60) Provisional application No. 60/583,251, filed on Jun. 25, 2004.

(51) Int. Cl.
*C12P 7/06* (2006.01)
*C12P 1/00* (2006.01)
*C12N 1/00* (2006.01)

(52) U.S. Cl. ............... 435/161; 435/41; 435/255.1; 435/255.2; 435/255.5

(58) Field of Classification Search ............... None
See application file for complete search history.

(56) References Cited

U.S. PATENT DOCUMENTS

| | | | |
|---|---|---|---|
| 2,916,142 A | 12/1959 | Fontein | |
| 3,029,169 A | 4/1962 | Dowie et al. | |
| 3,077,308 A * | 2/1963 | Tibor et al. | 241/11 |
| 3,236,740 A | 2/1966 | Smith et al. | |
| 3,264,113 A | 8/1966 | Berta et al. | |
| 3,474,722 A | 10/1969 | Watson et al. | |
| 3,477,855 A | 11/1969 | Freeman | |
| 3,909,288 A | 9/1975 | Powell et al. | |
| 4,069,103 A | 1/1978 | Muller | |
| 4,089,745 A | 5/1978 | Antrim et al. | |
| 4,144,087 A | 3/1979 | Chwalek et al. | |
| 4,181,748 A | 1/1980 | Chwalek et al. | |
| 4,234,614 A | 11/1980 | Hart | |
| 4,244,748 A | 1/1981 | Chwalek et al. | |
| 4,287,304 A | 9/1981 | Muller et al. | |
| 4,329,371 A | 5/1982 | Hart | |
| 4,361,651 A | 11/1982 | Keim | |
| 4,435,429 A | 3/1984 | Burrows et al. | |
| 4,448,881 A | 5/1984 | Muller et al. | |
| 4,461,648 A | 7/1984 | Foody | |
| 4,716,218 A | 12/1987 | Chen et al. | |
| 4,737,371 A | 4/1988 | Bookwalter | |
| 4,752,579 A | 6/1988 | Arena et al. | |
| 4,795,101 A | 1/1989 | Silver | |
| 4,810,647 A | 3/1989 | Monceaux et al. | |
| 5,846,787 A | 12/1998 | Ladisch et al. | |
| 6,090,595 A | 7/2000 | Foody et al. | |
| 2004/0187863 A1* | 9/2004 | Langhauser | 127/24 |

OTHER PUBLICATIONS

Abbadi, A., et al.; Study on Solid Acid Catalyzed Hydrolysis of Maltose and Related Polysacchardes; Starch/Stärke 50 (1998), Nr. 1. S. 23-28.
Anderson, P.J., et al; High Efficiency Carbohydrate Fermentation to Ethanol at Temperatures above 40° C by *Kluyveromyces marxianus* var. *marxianus* Isolated from Sugar Mills; Applied and Environmental Microbiology, (Jun. 1986), p. 1314-1320.
Barron, N., et al; Use of Carbohydrate-Supplemented Distillery Spent Wash As a Medium for Ethanol Production by a Thermotolerant Strain of Yeast at 45° C; Biotechnology Techniques (May 1996), vol. 10(5):349-352.
Bely, M., et al; Assimilable Nitrogen Addition and Hexose Transport System Activity During Enological Fermentation; J. Inst. Brew., (Jul.-Aug., 1994) vol. 100 p. 279-282.
Bentley, I.S., et al; Starch Conversion, Industrial Enzymology (2d Ed 1996) Ch. 2.20.
Biss, R., et al; The Significance of Insoluble Protein Solubilization in Corn Steeping; *Cereal Chem.* (1988) vol. 65, No. 4, p. 281-284.
Blessin, C.W., et al; Chemical Dehulling of Dent Corn; *Cereal Chem.* (May, 1970) vol. 47, p. 303-308.
Brekke, O.L.; Corn Dry Milling Industry; inCorn: Culture, Processing Products (1970) Ch. 14, p. 262-291.
Brown, A.J.; On the Existence of a Semi-Permeable Membrane Enclosing the Seeds of some of the Gramineae; Annals of Botany, (Jan. 1907) vol. 21(No. 81):80-87.
Brown, R.B., et al; Note on the Suitability for Wet Milling of Corn Exposed to High Drying Temperatures at Different Moisture Contents; *Cereal Chem.*; (1981) vol. 58(1):75-76.
Casal, M., et al; Effects of Ethanol and Other Alkanols on Transport of Acetic Acid in *Saccharomyces cerevisiae*; Applied and Environmental Microbiology (Feb. 1998) vol. 64(2):665-668.

(Continued)

*Primary Examiner*—Christopher R Tate
*Assistant Examiner*—Aaron J Kosar
(74) *Attorney, Agent, or Firm*—Dicke, Billig & Czaja, PLLC

(57) ABSTRACT

An improved method for processing corn into ethanol and other valuable co-products. The invention generally involves a multi-step process which produces germ (or oil), protein, and feed yeast as its co-products while maintaining or enhancing the provision of fermentable sugar to ethanol fermentation. This is accomplished by fundamentally altering the way the corn is fractionated, disrupting the cell walls rather than the protein matrix as is done in conventional wet milling.

21 Claims, 9 Drawing Sheets

OTHER PUBLICATIONS

Chang, D., et al.; Economic-Engineering Assessment of Sequential Extraction Processing of Corn; Transactions of the American Society of Agricultural Engineers (1995), vol. 38(4):1129-1138.

Chin, P.M., et al; Effect of Recycled Laboratory Backset on Fermentation of Wheat Mashes; J. Agric. Food Chem. (1993) vol. 41, p. 1158-1163.

Chung, B.H., et al.; On Fermentability of Nation Catalyzed Hemicellulose Hydrolyzates; Applied Biochemistry and Biochemistry; (Spring 1992) vol. 34-35: 125-129 (Abstract only).

Cox, M.J., et al.; Effect of the Sulfurous Acid Steep in Corn Wet Milling; *Cereal Chem*. (Nov. 1944) vol. 21(6):447-465.

Cysewski, G.R., et al.; Utilization of Cellulosic Materials through Enzymatic Hydrolysis. I. Fermentation of Hydrolysate to Ethanol and Single-Cell Protein; Biotechnology and Engineering (1976) vol. 18, p. 1297-1313.

Dailey, Jr., O.D., et al.; Influence of Lactic Acid on the Solubilization of Protein during Corn Steeping; J. Agric. Food Chem.; (2000) 48, 1352-1357.

Dickey, L.C., et al.; Hydrocyclone Separation of Dry-Milled Corn; (1997) *Cereal Chem*. 74(5):676-680.

Doner, L.W., et al.; Isolation of Hemicellulose from Corn Fiber by Alkaline Hydrogen Peroxide Extraction; (1997) *Cereal Chem*. 74(2):176-181.

Doner, L.W., et al.; Analysis and Properties of Arabinoxylans from Discrete Corn Wet-Milling Fiber Fractions; J. Agric. Food Chem. (2001) 49, 1266-1269.

Doner, L.W., et al.; Isolation and Characterization of Cellulose/Arabinoxylan Residual Mixtures from Corn Fiber Gum Process; *Cereal Chem*. (2001) 78(2):200-204.

Dowd, M.K., et al.; Low Molecular Weight Organic Composition of Ethanol Stillage from Corn; *Cereal Chem*. (1993) 70(2):204-209.

Eckhoff, S.R., et al.; Comparison Between Alkali and Conventional Corn Wet-Milling: 100-g Procedures; *Cereal Chem*. (1999) 76(1):96-99.

Foda, M.S., et al.; Production of *Candida utilis* on Slop By-Product of Fermentation Industries; Zbl. Bakt. Abt.II, Bd. (1976) 131, S. 512-516.

Grabber, J.H., et al.; Diferulate Cross-Links Impede the Enzymatic Degradation of Non-Lignified Maize Walls; J Sci Food Agric (1998) 77, 193-200.

Grohmann, K., et al.; Saccharification of Corn Fibre by Combined Treatment with Dilute Sulphuric Acid and Enzymes; Process Biochemistry; (1997), 32(5):405-415.

Hespell, R.B., et al.; Hydrolysis by Commercial Enzyme Mixtures of AFEX-Treated Corn Fiber and Isolated Xylans; Applied Biochemistry and Biotechnology; (1997) vol. 62 p. 87-97.

Hespell, R.B.; Extraction and Characterization of Hemicellulose from the Corn Fiber Produced by Corn Wet-Milling Processes; J. Agric. Food Chem. (1998) vol. 46, p. 2615-2619.

Hojilla-Evangelista, M.P.; Alternative Corn Fractionation Technology for Ethanol Production; *Cereal Chem*. (1992) 69(6):643-647.

Ingledew, W.M.; Yeasts for Production of Fuel Ethanol; The Yeasts ($2^{nd}$ Ed.,1993); p. 245-291.

Johnson, L.A., et al.; Wet Milling: The Basis for Corn Biorefineries; in Corn: Chemistry and Technology, ($2^{nd}$ Ed., 2003); Ch. 12, p. 449-495.

Kennedy, J.F., et al.; The Identification and Quantitation of the Hydroxycinnamic Acid Substituents of a Polysaccharide Extracted From Maize Bran; J Sci Food Agric (1999) 79:464-470.

Kim, S.B., et al.; Hydrolysis of Hemicellulose by Solid Superacid; Biotechnology and Bioengineering Symp. No. 15 (1985) p. 81-90.

Kosaric, N., et al; Growth of *Saccharomyce cerevisiae* in Stillage from Alcohol Fermentation of Jerusalem Artichokes; Process Biochemistry (Jun. 1989) p. 92-96.

Krishna, S. H., et al.; Simultaneous Saccharification and Fermentation of Lignocellulosic Wastes to Ethanol Using a Thermotolerant Yeast; Bioresource Technology; (2001) vol. 77, p. 193-196.

Krubasik, P., et al.; Molecular Evolution of Lyopene Cyclases Involved in the Formation of Carotenoids with Ionone End Groups; Biochemical Society Transactions (2000) vol. 28, part 6, p. 802-806.

Leathers, T.D., et al,; Saccharification of Corn Fiber Using Enzymes from *Auereobasidium* sp. Strain NRRLY-2311-1; Applied Biochemistry and Biotechnology; (1996) vol. 59, p. 337-347.

Lee, Y.Y., et al.; Dilute-Acid Hydrolysis of Lignocellulosic Biomass; Advances in Biochemical Engineering/Biotechnology; (1999) vol. 65, p. 92-115.

Lewis, S.M.; Fermentation Alcohol; in Industrial Enzymology $2^{nd}$ Ed., (1996) Ch. 2.1. p. 12-48.

Ling, D., et al.; Corn Wet Milling with a Commercial Enzyme Preparation; *Cereal Chem*. (1991) 68(2):205-206.

Lopes-Filho, J.F., et al.; Intermittent Milling and Dynamic Steeping Process for Corn Starch Recovery; *Cereal Chem*. (1997) 74(5):633-638.

Maisch, W.F.; Fermentation Processes and Products; in Com: Chemistry and Technology ($2^{nd}$ Ed., 2003); Ch. 19, p. 695-720.

Maleszka, R., et al.; Fermentation of D-xylose, xylitol, and D-xylulose by Yeasts; Can. J. Microbiol.; (1982) vol. 28, p. 360-363.

Maiorella, Brian, et al.; By-Product Inhibition Effects on Ethanolic Fermentation by *Saccharomyces cerevisiae*; Biotechnology and Bioengineering; (1983) vol. 25 p. 103-121.

Maiorella, B.L., et al.; Distillery Effluent Treatment and By-Product Recovery; Process Biochemistry, (Aug. 1983) p. 5-12.

Margaritis, A., et al; Direct Fermentation of D-Xylose to Ethanol by *Kluyveromyces marxianus* Strains; Applied and Environmental Microbiology, (Nov. 1982) 44(5):1039-1041.

Martinez, A., et al.; Effects of $Ca(OH)_2$ Treatments ("Overliming") on the Composition and Toxicity of Bagasse Hemicellulose Hydrolysates; Biotechnology and Bioengineering (2000) 69(5):526-536.

Martinez, R., et al.; Kinetic Approach to Nixtamalization of Corn Pericarp; *Cereal Chem*. (2001) 78(2):107-110.

Mauricio, J.C., et al.; Apparent Loss of Sugar Transport Activity in *Saccharomyces Cerevisiae* May Mainly Account for Maximum Ethanol Production During Alcoholic Fermentation; Biotechnology Letters (Jul. 1992) 14(7):557-582.

Mistry, A.H., et al.; Dry Milling and Physical Characteristics of Alkali-Debranned Yellow. Dent Corn; *Cereal Chem*. (1992) 69(1):82-84.

Mistry, A.H., et al.; Fractionation of High-Lysine Corn to Produce Edible By-Products; *Cereal Chem*. (1992) 69(4):433-435.

Moreau, R.A.; Comparison of Yield and Composition of Oil Extracted from Corn Fiber and Corn Bran; *Cereal Chem*. (1999) 76(3):449-451.

Morgan, A.I., et al.; Peeling Grain; Food Technology (Aug. 1964) either p. 40-43.

Mosier, N., et al.; Bioprocess and Metabolic Engineering Technologies for Biofuels and Value-Added Coproducts; American Institute of Chemical Engineers Annual Meeting; Nov. 21, 2003; (Abstract Only).

Myers, D.J., et al.; Functional Properties of Protein Extracted from Flaked Defatted, Whole Corn by Ethanol/Alkali During Sequential Extraction Processing; JAOCS (Nov. 1994) 71(11):1201-1204.

Neryng, A., et al.; Laboratory Wet Milling of Ensiled Corn Kernels; *Cereal Chem*. (1984) 61(1):8-14.

Pampulha, M.E., et al.; Interaction of the Effects of Acetic Acid and Ethanol on Inhibition of Fermentation in *Saccharomyces Cerevisiae*; Biotechnology Letters (1989) 11(4):269-274.

Peppler, H.J.; The Yeasts ( $2^{nd}$ Ed.,1993); Ch. 8. 421-461.

Pomeranz, Y.; The Problems Involved in "Peeling" of Wheat Kernels; Cereal Science Today; (Mar. 1961) 6(3):76-79.

Randolph, L.F.,; Development Morphology of the Caryopsis in Maize; Journal of Agricultural Research; (1936) 53(12):881-916.

Ronkainen, P., et al.; The Re-Use of Stillage Water in the Mashing of Grain as a Means of Energy Conservation; J. Inst. Brew., (Mar.-Apr. 2978) vol. 84 p. 115-117.

Rooney, L.W., et al.; Food use on Whole Corn and Dry-Milled Fractions; in Corn: Chemistry and Technology, ($2^{nd}$ Ed., 2003); p. 495-535.

Saha, B.C., et al.; Pretreatment and Enzymatic Saccharification of Corn Fiber, Applied Biochemistry and Biotechnology (1999) vol. 76, p. 65-77.

Sahai, D., et al.; Assessing Degree of Cook During Corn Nixtamalization: Impact of Processing Variables; *Cereal Chem.*; (1999) 76(6):850-854.

Sahai, D., et al.; Dry Matter Loss During Nixtamalization of a White Corn Hybrid: Impact of Processing Parameters; *Cereal Chem.* (1999) 77(2):254-258.

Sahai, D., et al.; Alkaline Processing (Nixtamalization) of White Mexican Corn Hybrids for Tortilla Production: Significance of Corn Physicochemical Characteristics and Process Conditions; *Cereal Chem.* (2001) 78(2):116-120.

Saulnier, L., et al.; Studies of Polysaccharides Solubilized During Alkaline Cooking of Maize Kernels; Journal of Cereal Science (1993) vol. 17 p. 267-276.

Saulnier, L., et al.; Isolation and Partial Characterization of Feruloylated Oligosaccharides from Maize Bran; Carbohydrate Research (1995) vol. 272 p. 241-253.

Saulnier, L., et al.; Cell Wall Polysaccharide Interactions in Maize Bran; Carbohydrate Polymers (1995) vol. 26 p. 279-287.

Saulnier, L., et al.; Ferulic Acid and Diferulic Acids as Components of Sugar-Beet Pectins and Maize Bran Heteroxylans; J Sci Food Agric (1999) 79:396-402.

Seckinger, H.L.; Hemicelluloses of the Cementing Layer and of Some Cell Walls of the Corn Kernel; *Cereal Chem.*; (Mar. 1960) vol. 37 p. 121-128.

Shandera, D.L., et al.; Interactions of Sulfur Dioxide, Lactic Acid, and Temperature During Simulated Corn Wet Milling; *Cereal Chem.*; (1995) 72(4):371-378.

Singh, N., et al.; Hydrocyclones in the Corn Wet Milling Industry; *Cereal Chem.*; (Aug. 1996) 41(8):676-679.

Singh, V., et al.; Effect of Soak Time, Soak Temperature, and Lactic Acid on Germ Recovery Parameters; *Cereal Chem.*; (1996) 73(6):716-720.

Singh, S.K., et al.; Effect of Sodium Hydroxide, Calcium Hydroxide, and Potassium Hydroxide on Debranning of Corn; *Cereal Chem.*; (1997) 74(3):254-257.

Singh, V., et al.; Economics of Germ Preseparation for Dry-Grind Ethanol Facilities; *Cereal Chem.*; (1997) 74(4):462-466.

Singh, V., et al.; Batch Steeping of Corn: Effects of Adding Lactic Acid and Sulfur Dioxide at Different Times on Starch Yields, Protein Contents and Starch Pasting Properties; *Cereal Chem.*; (1999) 76(5):600-605.

Singh, V., et al.; Effect of Corn Oil on Thin Stillage Evaporators; *Cereal Chem.*; (1888) 76(6):846-849.

Singh, V., et al.; Recovery of Fiber in the Corn Dry-Grind Ethanol Process: A Feedstock for Valuable Coproducts; *Cereal Chem.*; (1999) 76(6):868-872.

Singh, V., et al.; Effect of Various Acids and Sulfites in Steep Solution on Yields and Composition of Corn Fiber and Corn Fiber Oil; *Cereal Chem.*; (2000) 77(5):665-668.

Singh, V., et al.; Hybrid Variability and Effect of Growth Location on Corn Fiber Yields and Corn Fiber Oil Composition; *Cereal Chem.*; (2000) 77(5):692-695.

Singh, V., et al.; Effect of Alternative Milling Techniques on the Yield and Composition of Corn Germ Oil and Corn Fiber Oil; *Cereal Chem.*; (2001) 78(1):46-49.

Sreenath, H.K., et al.; Enzymic Saccharification of Alfalfa Fibre after Liquid Hot Water Pretreatment; Process Biochemistry (1999) vol. 35 p. 33-41.

Sreenath, H.K., et al.; Ethanol Production From Alfalfa Fiber Fractions by Saccharification and Fermentation; Process Biochemistry (2001) vol. 36 p. 1199-1204.

Stambuk, B.U., et al.; D-Xylose Transport by *Candida succiphila* and *Kluyveromyces marxianus*; Applied Biochemistry and Biotechnology; (2003) vol. 105-108 p. 256-263.

Steinke, J.D., Steeping Maize in the Presence of Mualtiple Enzymes. I. Static Batchwise Steeping; *Cereal Chem.*; (1991) 68(1):7-17.

St. Julian, G., et al.; Glycerol Accumulation While Recycling Thin Stillage in Corn Fermentations to Ethanol; Journal of Industrial Microbiology; (1990) vol. 5 p. 391-394.

Streclar, L., et al.; Corn Oil; Baileys Industrial Oil and Fat Products, vol. 2; (1995) p. 125-157.

Taylor, F., et al.; Dry-Grind Process for Fuel Ethanol by Continuous Fermentation and Stripping; Biotehnol. Prog.; (2000) 16(4):541-547.

Taylor, F., et al.; Fermentation and Costs of Fuel Ethanol from Corn with Quick-Germ Process; Applied Biochemistry and Biotechnology; (2001) vol. 94, p. 41-49.

Tucker M.P., et al.;, Conversion of Distiller's Grain into Fuel Alcohol and a Higher Value Animal Feed by Dilute-Acid Pretreatment; Appl Biochem Biotechnol. (Spring 2004); 113-116:1139-59.

Tumbleson, M., et al.; Modified Dry Grind Ethanol; University of Illinois; (Mar. 2001) p. 1-55.

Wahjudi, J., et al; Quick Fiber Process: Effect of Mash Temperature, Dry Solids, and Residual Germ on Fiber Yield and Purity; *Cereal Chem.*; (2000) 77(5):640-644.

Wang, D., et al.; Effect of Broken Corn Levels on Water Absorption and Steepwater Characteristics; *Cereal Chem.*; (2000) 77(5):525-528.

Wang, L., et al.; Studies on the Utilization of Molasses Alcohol Slops; Journal of the Chinese Agricultural Chemical Society; (Jun. 1980) 18(1-2):25-33.

Watson, S.A.; Corn and Sorghum Starches: Production; in Starch Chemistry & Technology; (1984) Ch. 12 p. 417-468.

Watson, S.A.; Description, Development, Structure and Composition of the Corn Kernel; in Corn: Chemistry and Technology, ($2^{nd}$ Ed., 2003); Ch. 3 p. 69-105.

Weil, J.R., et al.; Pretreatment of Corn Fiber by Pressure Cooking in Water, Applied Biochemistry and Biotechnology; (1998) vol. 73 p. 1-17.

Wolf, M.J., et al.; Preparation and Some Properties of Hemicelluloses from Corn Hulls; *Cereal Chem.*; vol. 30, p. 451-470, (1953).

Wolf, M.J., et al.; Composition of the Cementing Layer and Adjacent Tissues as Related to Germ-Endosperm Separation in Corn; *Cereal Chem.*; (1957) vol. 35 p. 127-136.

Yang, P., et al.; Effects of Alkali Debranning, Roller Mill Cracking and Gap Setting, and Alkali Steeping Conditions on Milling Yields from a Dent Corn Hybrid; *Cereal Chem.*; (2000) 77(2):128-132.

Yang, P., et al.; Reducing Steep Time by Adding Lactic Acid During Countercurrent Steeping of Corn with Different Initial Moisture Contents; *Cereal Chem.*; 77(5):529-534, (2000).

* cited by examiner

CORN FRACTIONATION METHOD

CROSS-REFERENCE TO RELATED APPLICATIONS

This application claims the benefit of U.S. Provisional Patent Application 60/583,251, filed Jun. 25, 2004, and is a continuation-in-part of U.S. patent application Ser. No. 10/877,451, filed Jun. 25, 2004.

FIELD OF THE INVENTION

This invention concerns methods for processing corn into ethanol and other valuable co-products.

BACKGROUND

Ethanol is useful as a fuel extender, octane enhancer, and pollution-suppressing oxygenate for blending with gasoline. It is also useful as an industrial solvent, chemical intermediate, and, when suitably pure, as a beverage component. Ethanol can be produced from a variety of raw materials, but in the US the majority is produced by fermentation of grain, particularly corn (maize). Fuel ethanol production supports corn prices, diversifies our national energy base, promotes cleaner air, provides good jobs in rural areas, and returns profits directly to the farmer-owners of ethanol cooperatives. The US ethanol industry currently has 2.85 billion gallons/year (gpy) of installed capacity in 73 plants.

Ethanol is currently produced from corn by two processes, dry-grind and wet-milling. The dry-grind process, adapted from beverage alcohol production, fine-grinds the entire corn kernel, saccharifies and ferments the starch, distills off the ethanol from the unfractionated mash, and dries the residual product to make an animal feed, Distillers Dried Grain and Solubles (DDGS). DDGS suffers from oversupply and declining prices. Wet milling first separates the corn into its major components: starch, germ, protein, and fiber by steeping, wet-grinding, sieving, and density separation. Germ is processed for oil recovery, protein is dried as a premium feed ingredient, and the starch is saccharified and fermented for ethanol production. The fiber is combined with the concentrated steepwater and dried to produce corn gluten feed. This roughage feed product sells at an even lower price than DDGS. Wet mills get more revenue from co-products than do dry-grind plants, but incur higher capital and energy costs. Roughly half of the US installed ethanol capacity is wet milling but most of the new mills are dry grind.

Two processes in now-expired patents disclose protein recovered from hydrolyzed endosperm. A patent by Keim (U.S. Pat. No. 4,361,651) discusses primarily a process using starch from an abbreviated wet milling process. Germ is removed conventionally, then the remaining mash is diluted and saccharified, and fiber and protein fractions are recovered from the resulting sugar solution with screens and centrifuges. A de-starched gluten of 80% protein content is produced. Muller and Miller (U.S. Pat. No. 4,448,881) describe a similar process starting with dry-milled starch. Both processes employ conventional dry or wet milling techniques and produce a high-fiber product; neither addresses removal of fermentation by-products from recycled water.

Other alternative corn fractionation technologies have been proposed at various times; some are under study or development in other organizations. The short-steep process, also known as "Quick Germ" and "Quick Fiber," begins as wet milling using a short steep with reduced chemical addition or none at all. After germ isolation, conventional fermentation gives ethanol and low-oil distillers grains. Fiber can be isolated before fermentation for production of corn fiber oil or corn fiber gum. Alkali wet milling employs an alkaline de-branning followed by alkaline disruption of the endosperm. It is believed that it is being developed for starch production rather than ethanol production.

The Sequential Extraction Process, which uses ethanol to extract oil and protein, is quite capital intensive and requires production of a protein product intended for human food use in order to be economic. Its intent is thus quite different than that of the invention. There continues to be private interest in using dry milling technology as used in production of corn meal and grits to separate the germ ahead of the fermentation.

SUMMARY OF THE INVENTION

The invention is an improved method for processing corn into ethanol and other valuable co-products. Corn is first separated into components, such as by de-braning by an advanced, proprietary alkaline de-branning process, and the separated bran material is hydrolyzed to give free sugars (pentoses and hexoses). The separated corn may be gently crushed or broken by controlled impact (or controlled rolling), the germ may be isolated by flotation, and the endosperm may be hydrolyzed with amylase. A largely insoluble protein fraction is isolated from the hydrolysate, treated to reduce the soluble and colloidal fiber content, and preferably dried for sale as a high-grade feed ingredient. Sugars from the starch hydrolysis are fermented to ethanol, along with glucose and other hexoses (e.g., galactose) from the cell wall hydrolysate. Yeast is isolated from the spent beer before distillation. Still bottoms containing pentoses, cellobiose, and fermentation by-products are sent to a second, aerobic fermentation where the solubles are converted to additional yeast. The resulting water may be recycled to the process without buildup of inhibitory organic acids. Decreased dryer load and internal by-product reuse will decrease energy use and VOC emissions.

The inventive method disrupts the cell walls while avoiding attacking the protein matrix as in wet milling. No steeping is involved. This solubilizes much less of the initially insoluble endosperm protein, preserving its value and lowering processing cost. Protein is isolated from the saccharified or dextrinized endosperm before fermentation, corn is de-branned for easier protein separation and to concentrate the bran for economical hydrolysis, and pentoses and fermentation by-products are consumed in growing secondary yeast. Combining fermentation yeast and secondary yeast streams decreases the unit cost of yeast harvest.

The invention is distinct from conventional processes in that, by converting a large part of the fiber into fermentable sugar, it avoids producing DDGS, and also in that it isolates a high value protein concentrate. The invention does not employ a capital-intensive steeping process or require specialized wet-mill grinding equipment. The invention uses substantially less sodium hydroxide in any de-branning step, and does not employ base in the disruption of the endosperm. The invention recovers protein differently than alkali wet milling, and specifically addresses integration with the fermentation, fiber conversion, and water recycle.

BRIEF DESCRIPTION OF THE DRAWINGS

FIG. 2A illustrates initial separation employing alkaline debranning.
FIG. 2B illustrates initial separation employing short-steep wet milling and dry bran separation.
FIG. 2C illustrates initial separation by dry milling.

FIG. 3A illustrates sequential hydrolysis with acid and enzymes, including an optional fiber recycle step to increase residence time. FIG. 3B illustrates acid-enzyme hydrolysis with separation of cellulose fibers for separate enzyme treatment, and also hydrolysis of soluble pentosans using a solid catalyst. FIG. 3C illustrates separation of cellulose fibers for separate enzyme treatment, and also hydrolysis of soluble pentosans with acid recovery by electrodialysis.

FIG. 4A illustrates distillation with pre-separation of yeast by centrifugation, and a separate stripper to remove ethanol from yeast. FIG. 4B illustrates separation of yeast by tangential-flow filtration and diafiltration.

DETAILED DESCRIPTION

Figure 1:
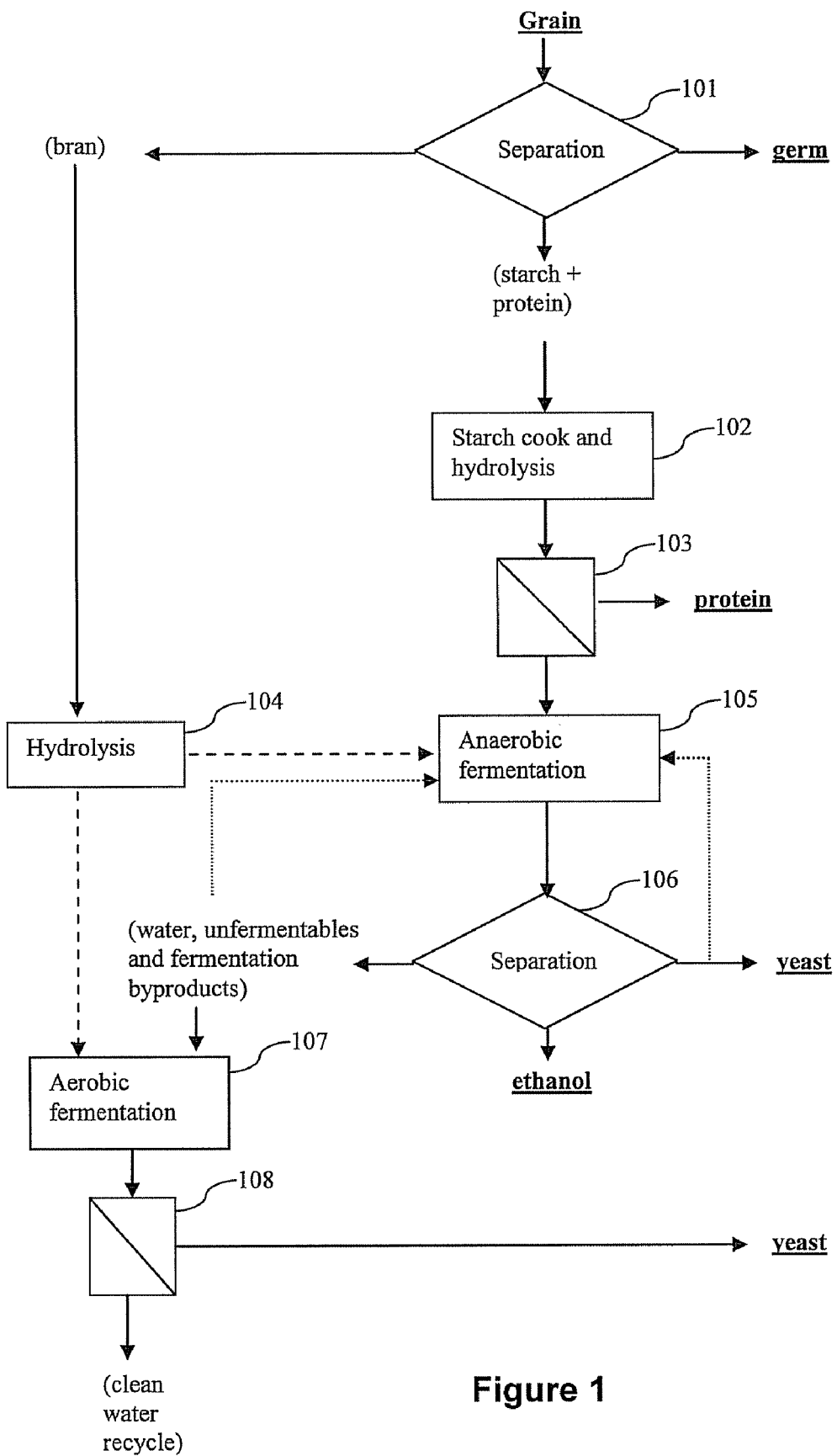
FIG. 1 illustrates the overall process scheme.

The figures are schematic flowcharts illustrating particular embodiments of one or more portions of the invention. There are many main components to the invention, some of which are optional but so desired that they are shown in the figures in the same manner as the required components. However, it should be understood that this is done by way of illustration and not limitation on the scope of the invention.

The value of Distillers Dried Grains and Solubles (DDGS), the principal co-product of dry-grind ethanol production, is depressed due to market saturation. Almost half the industry capacity and the majority of the farmer-owned portion is dry-grind, reflecting the substantial expansion of that segment in recent years. 555 million gallons of dry grind capacity is currently under construction in 14 plants. This increased capacity will exacerbate the problem of DDGS market saturation. An alternative to DDGS production is badly needed. Published pricing data clearly show that the non-starch components of the corn are worth more separately than when they are co-mingled as they are in distillers grains. Wet mill operations realize a portion of this available value, but it is eaten up by the higher capital and energy costs of wet milling. The invention separates the non-starch components of the corn so that they can be sold to best advantage, while maintaining ethanol production and without incurring the substantial additional costs involved in wet milling.

Ethanol is the largest volume product of a grain distillery and (with reasonable cost allocations) the most profitable. One advantage of this invention is to maintain or enhance ethanol production relative to the dry-grind process.

High-fiber co-products such as DDGS and corn gluten feed are largely though not entirely restricted to feeding ruminants, and do not command a high value relative to the corn from which they were produced. Another advantage of this invention is to provide a co-product mix such that all co-products sell for substantially greater value than the starting corn on a weight basis.

In order to avoid producing a high-fiber product, another advantage of this invention is to convert most of the corn fiber into other, more valuable chemical forms.

Conventional wet milling produces a valuable protein product, corn gluten meal, from the insoluble endosperm proteins of the grain. The amount of corn gluten meal produced is less than half the insoluble protein in the starting endosperm, because wet milling disrupts the protein matrix by chemical action of sulfurous acid, in order to release the starch. Another advantage of this invention is the production of one or more insoluble protein products with increased yield.

Corn germ contains the majority of the oil in the corn kernel. Corn oil is a high-quality vegetable oil valued as an ingredient and a frying fat. The spent germ after oil removal contains protein with good amino acid balance and is a valuable animal feed. Another advantage of the invention is the production of corn oil.

Ethanol fermentation produces a variety of low-molecular weight by-products including glycerol and organic acids. These substances inhibit fermentation if allowed to accumulate, making product drying more difficult because of their hygroscopic nature, and contributing to air pollution when they evaporate in the product dryers. One advantage of this invention is the removal of low molecular weight soluble organics from the water stream, thereby permitting increased water recycling within the process and decreasing the amount of these substances entering the dryers.

Yeast is a valuable feed ingredient, containing high quality protein, highly digestible phosphorus, and vitamins, and is valued as a palatability enhancer. Yeast harvested in a metabolically active state can also be used to prepare yeast autolysates which find application in flavorings and as fermentation nutrients. Another advantage of this invention is enhanced production of valuable yeast products.

Ethanol production remains an energy-intensive process even though modern dry-grind plants are much more efficient than those of the past. Another advantage of this invention is decreased energy consumption relative to modern dry-grind plants.

The invention is a multi-step process which produces germ (or oil), protein, and feed yeast as its co-products while maintaining or enhancing the provision of fermentable sugar to ethanol fermentation. This is accomplished by fundamentally altering the way the corn is fractionated, disrupting the cell walls rather than the protein matrix as is done in conventional wet milling. Substantially all of the products have more value than the input corn; no low-value roughage feed product is produced.

The corn is first de-branned, preferably but not necessarily using a novel proprietary alkaline debranning process. The preferred process is a major improvement since the nutrient-rich aleurone stays with the endosperm (unlike wet milling and mechanical debranning) and the chemical consumption is much reduced in comparison with previous alkaline processes. The pericarp fiber goes through a succession of treatments where the majority of the structural carbohydrate polymers are converted to free sugars which are sent to fermentation. The process may be operated so that glucose is sent primarily to the primary fermentation for ethanol production and pentoses to the secondary fermentation for yeast production, or if desired both streams may be sent to either fermentation. Optionally, a small amount of material including tip cap and unconverted fiber can be removed at this point. This small fraction can be composted or used for fuel.

The remainder of the corn is disrupted by mechanical and enzymatic treatments. The germ is isolated in much the same way as in wet milling. The starch is converted to fermentable sugar with heat and amylase as in any ethanol process and the protein is separated from the resulting sugar stream before fermentation. Fermentation is largely conventional but, because yeast is recovered and sold, there is no incentive to limit yeast production. In normal alcoholic fermentation, limitation of assimilable nitrogen sources such as ammonia induces a marked slowing of the fermentation mediated by decreased sugar uptake. Therefore it is advantageous to continue to feed ammonia or other sources of nitrogen throughout the process. After fermentation, yeast is recovered from the fermentation stream before distillation. This is practical because all other particulate components have been previously removed. When the fermentation is operated to maintain viability, some of the yeast can be recycled to the fermentation to speed the process.

After ethanol recovery, the still bottoms (combined with the pentose stream if the latter was previously separated) are sent to a second, aerobic fermentation step where unfermented sugars (including residual glucose, pentoses and cellobiose) and fermentation by-products are converted to additional yeast. This yeast is recovered and combined with the recovered fermentation yeast for drying, providing improved economies of scale. Water is recycled to the process without accumulation of inhibitory organic acids. Since no concentrated solubles stream is sent to the dryers, there is less VOC emission from the dryers. Energy savings in the process arise primarily from decreased dryer load, and secondarily from decreased volume passing through the stripper.

The above scheme is efficient and preferable for many installations, but it will be apparent to those skilled in the art that variations are possible without altering the fundamental nature of the invention. Some of these variations result from use of alternative technologies for certain steps, some result in alteration in the order of certain steps, and some may be preferable in certain instances for cost or other reasons. For example, the degerming and debranning could be accomplished by dry processes known to the art, or by a modified wet-milling process which isolates germ and bran together, then separates them by aspiration after drying. Oil could be isolated from the germ on-site and the spent germ could be added to the fiber stream. The primary and secondary yeast could be kept separate, perhaps processed on the same equipment but in alternation instead of as a mixture. All or part of the protein product could be left in through the fermentation and isolated with the yeast from the primary fermentation, or the protein product could be blended with the isolated yeast, to make a combined feed with good amino acid balance. A low-temperature amylase digestion could be employed to convert the starch to sugars. These and other modifications could be realized without altering the fundamental nature of the invention.

FIG. 1 is a schematic flowchart of the overall scheme of the invention. In the following description, values of numeric parameters should be understood as preferred and not required embodiments of the invention, unless such values appear in the claims.

In step 101, grain is subjected to a set of initial processing and separation steps resulting in the production of three streams: a bran stream comprising primarily pericarp, an endosperm stream comprising the bulk of the protein and starch content of the grain, and a germ stream which constitutes a valuable product.

Preferably, the pericarp is first removed from the grain by any suitable method. Ideally, this method selectively removes the pericarp, leaves the nutrient-rich aleurone with the endosperm, and does not cause loss of fermentable starch as occurs in wet milling. A preferred alkaline debranning method is described in U.S. provisional patent application No. 60/482,894, filed Jun. 25, 2003, and subsequent co-pending U.S. patent application Ser. No. 10/877,451, filed Jun. 25, 2004, which was published as U.S. Patent Application Publication 2005/0025868A1 and is incorporated by reference in its entirety into this application. Other methods which substantially remove the pericarp and desirably meet the other objectives of the invention could also be used.

Next, the endosperm is disrupted to release the germ and particulate endosperm solids. Suitable methods include impact disruption with an Entoleter or similar impact device, disk milling with a Bauer-type mill, roller milling with flaking rolls or finely serrated rolls, with or without additional or enzymatic disruption of the endosperm. Although large fragments of broken germ, if produced, can be recovered in good yield in subsequent steps, a process which leaves the germ largely intact is preferable. Depending on the moisture content of the corn leaving the preceding step and the disruption method employed, some water may be added so that it is absorbed by the corn before any mechanical disruption step. Increased moisture content serves to soften the endosperm and toughen the germ. Unlike wet milling, exposure to added water is brief and no steepwater is produced. If enzymatic action is employed to disrupt the endosperm or to help free the germ from adherent starch, the enzymes chosen are preferably low in proteolytic activity to avoid loss of hydrolyzed or solubilized proteins in subsequent steps. The most effective enzyme combinations generally include xylanase and/or cellulase enzymes produced by *Apergillus* and by a fungus of another genus such as *Trichoderma*, and include at least one enzyme produced on a complex substrate. This observation implies that a variety of specificities are necessary and that "side activities" including debranching activities, esterases, etc, are limiting rather than the xylanase or cellulase activities per se.

Third, the germ is isolated. This can be accomplished in a wet process by density flotation in a hydrocyclone, followed by sieving to separate the germ from excess starch. Here and elsewhere effective washing of the product is strongly preferred both for maintaining product concentration and to return fermentable material to the process. This germ recovery step is substantially similar to the conventional process employed in wet milling except that the necessary suspension density is somewhat higher on account of the higher density of the unsteeped germ. The density medium is provided by free starch granules and fine endosperm fragments including a portion recycled within the process. If pericarp was not removed or fully recovered initially it will be enriched in the germ fraction, along with aleurone fragments. Dry germ and bran separation using sieving, air tables, and/or air classifiers is an alternative to earlier separation of the bran.

In step 102, the endosperm stream is subjected to hydrolysis by acid or amylase to convert the starch to soluble dextrins or sugars while leaving the protein largely intact and insoluble. This stage is preferably preceded by a regrind step, to limit maximum particle size, preferably less than 1.5 mm, more preferably less than 1.0 mm, and in some cases depending on the equipment employed for starch conversion and protein recovery <0.5 mm. This regrind should preferably employ equipment which is intrinsically size selective so that primarily or only the oversize particles are ground. Examples include a roller mill or a disk (Bauer-type) mill. Less preferably a wet hammer mill such as a Fitzmill or a Reitz Disintegrator or an impact mill such as an Entoleter or pin mill can be employed. Starch cooking and hydrolysis may be accomplished by any of the techniques commonly employed in alcohol production: one-stage or two-stage amylase digestion in continuous or batch cookers, or acid thinning followed by amylase digestion. Preferably, this step is carried out to give full solubilization of the starch and minimum viscosity of the hydrolysate while securing sufficient reduction in molecular weight of the starch that it is not retained by any membranes employed in the subsequent protein isolation and has no tendency to form gel layers on the membrane surface. Preferably this step is performed under conditions which minimize the formation of retrograde starch and other refractory starch forms. In one preferred sequence the starch is treated continuously with a thermostable alpha amylase at a temperature between 85 and 95 C. Details of time, temperature, pH, and free calcium concentration will depend on the particular enzyme employed, and it is within the skill of the art to choose them, e.g., by experiment. Following this step, when the starch is well solubilized and largely broken down to oligosaccharides, the temperature is increased to 105-108 C for a period of 10-30 minutes to break down starch-lipid complexes and hydrolyze the starch thereby released. The amylase may not be stable under the latter conditions, so the heat step is carried out at the end of the starch conversion. Alternatively, a conventional starch cook with steam jet cooking and a split addition of amylase before and after the jet cooker may be employed according to techniques known in the art. If jet cooking is employed the maximum particle size chosen must be sufficiently small to prevent clogging of the steam-mixing valve. If a mechanically gentle process such as continuous pressure cooking is employed the maximum particle size may be set by the requirements for efficient starch release from the particles.

In step 103, the bulk of the insoluble protein is removed to make a valuable product. Isolation of one or two protein fractions from the starch hydrolysate leaves a solution of fermentable sugars. This step may employ microfiltration, ultrafiltration, gravity sedimentation, conventional filtration or centrifugation, alone or in combination. If filtration is employed, it is best done at elevated temperatures to minimize the viscosity of the filtrate and boost starch solubility. Pressure or vacuum filters may be employed but pressure filtration has the advantage that higher temperatures can be maintained. The protein fraction contains two components: one of large particle size, light color, and spongy texture, and a second of smaller particle size and deep golden color, similar to conventional corn gluten. These protein fractions are valuable as ingredients and as a raw material for isolation of zeins. They may be isolated together or separately. To isolate them together, the filter or other similar recovery device must be operated so that the fine particles are entrained in the interstices of the filter cake; this may require a finer particle size and thicker cake than would otherwise be necessary. Alternatively, both fractions may be isolated together using a suitable centrifuge of sufficient capacity. To isolate the two fractions separately, the coarse fraction may be recovered by filtration or sieving with the fine particles then isolated from filtrate and washings of the coarse fraction using tangential flow membrane filtration or disk centrifugation.

Optionally the endosperm fiber may be hydrolyzed by enzyme action so that it is not retained in the protein isolation process but passes on along with the starch-derived sugars.

To obtain higher protein content and greatest recovery of fermentable sugars the large protein fraction must be washed with water, for instance by washing the filter cake with water sprays, and/or by re-suspending the cake in water and then re-isolating the solids. It will be appreciated that this washing will be most efficient if it is conducted in stages, in countercurrent fashion, and if the cake is extensively dewatered between stages.

In step 104, the bran stream is subjected to pretreatment hydrolysis by some combination of agents including heat, acid and suitable enzymes resulting in the conversion of the bran polysaccharides to free sugars largely comprising monosaccharides and optionally disaccharides, depending on the metabolic capabilities of the organisms employed in the fermentation. This block of steps may optionally include a separation such that the hexoses are largely directed to the anaerobic fermentation and the pentoses to the aerobic fermentation, or else all or part of the unfractionated stream may be directed to either fermentation. A suitable process was described by Grohman and Bothast who used mild acid hydrolysis to increase the enzymatic susceptibility of corn pericarp polysaccharides, followed by treatment with commercial cellulase enzyme preparations. A similar process disclosed in U.S. Pat. No. 4,752,579 exploits the solubilization of the pentosan of partial hydrolysis to effect a separation of cellulose (which yields glucose on further hydrolysis) from pentoses by simple filtration, thereby permitting the glucose to be sent to one use while the pentoses, after further hydrolysis, are sent to a different destination. In this case it is preferred to send the cellulose, after hydrolysis by cellulase, to the anaerobic fermentation to increase ethanol production, while the solubilized pentosan oligosaccharides are sent first to further hydrolysis to release monosaccharides, then to the aerobic fermentation stage for production of yeast biomass. Hydrolysis of the pentoses may be accomplished by further acid hydrolysis using soluble acid, by acid hydrolysis using strongly acidic cation exchange resin in the hydrogen form or other solid acid as catalyst, or by enzymatic hydrolysis. An acid-recovery process may optionally be included in this stage, after further acid hydrolysis or prior to enzyme hydrolysis.

Having the pentoses bypass the primary fermentation contributes to biological stability since there is less substrate for any lactic acid bacteria present. However, recombining the pentose and cellulose streams by resuspending the cellulose in the pentosan hydrolysate improves water balance in the process since additional water is not needed for the cellulose resuspension. A solid-liquid separation may be employed after the cellulose digestion, and the solids containing unconverted cellulose and other refractory solids may be recycled for further hydrolysis or discarded.

In step 105, the sugars derived from the endosperm starch and optionally the fermentable sugars derived from the bran are fermented to ethanol by yeast or other suitable organisms. The starch-derived sugars are fermented to ethanol by the action of yeast, for instance *Saccharomyces cerevisiae* of any strain commonly employed for alcohol production. Suitable strains include Alltech brand alcohol yeast and Red Star brand bakers yeast. Any of the batch or continuous processes commonly employed in alcohol industry may be employed with little modification. Preferably, ammonia or other nitrogen source is fed continuously throughout the fermentation. Optionally, hydrolysates of the bran and endosperm fibers are added back to the process stream at this point in order to convert any glucose content to ethanol, to utilize any hydrolyzed protein or other nutrients in those fractions, and to provide additional time for enzyme action on the fiber oligosaccharides. Optionally, live yeast recovered from the fermentation stream before distillation may be recycled to the fermentation. Optionally a bed of immobilized yeast may be employed to carry our all or part of the fermentation.

In step 106, the fermentation broth is fractionated to give ethanol, yeast (or other biomass) and an aqueous fraction containing unfermentable sugars, fermentation by-products such as glycerol and organic acids, and other soluble materials derived from the grain or yeast. Optionally part of the yeast can be recycled to step 105, while the remainder constitutes a valuable product. Yeast is isolated from the resulting beer by any established process such as cross-flow microfiltration or continuous centrifugation. Small amounts of ethanol remaining in the yeast stream can be removed by vacuum flashing, by aeration so they are consumed by the yeast, by countercurrent stripping with steam or $CO_2$, or by a combination of steps. Optionally, a portion of the living yeast is recycled to the fermentation to permit a faster and more complete fermentation. The remaining yeast can be heat dried to make a valuable feed supplement, or if the fermentation and isolation has been conducted with care to preserve viability they can be subjected to autolysis by known methods to prepare valuable yeast autolysates and by-products. Optionally, yeast can be recovered from the still bottoms instead of ahead of the distillation, although this option loses the advantage of recycling yeast to the fermenter, the potential to make yeast autolysate, and possibly some nutritional quality from the yeast.

Conventional stripper-rectifier systems are suitable. If desired, the process is also adaptable to continuous stripping processes such as the Vacu-ferm process or the Taylor-USDA $CO_2$ stripping process or to pervaporation processes.

In step 107, all or part of the aqueous stream from step 106 (and any bran hydrolysate from step 104 which was not sent to step 105) is subjected to aerobic fermentation such that the bulk of the fermentation by-products (particularly organic acids) and unfermentable sugars are consumed with production of yeast or other biomass. Optionally, part of the aqueous stream from step 106 is recycled to step 105 as a source of makeup water or nutrients as is done in some conventional ethanol production (termed "backset").

If the fiber sugar stream was not combined with the main stream for the initial fermentation it is combined with the still bottoms at this time. Preferably this fermentation is conducted in a continuous fashion with vigorous aeration. Equipment of the airlift type is particularly suitable due to economical operation and simple construction, but conventional air-sparged, stirred tank and Waldhoff type units can also be employed provided adequate aeration is maintained and the culture is kept free of contamination. Cell recycling to the fermentation is desirable to permit high substrate conversions with short liquid residence times (and thus smaller, less expensive equipment). For secondary yeast production this is readily achieved using a continuous centrifuge or a ceramic or stainless steel membrane filter in cross-flow operation. A variety of organisms can potentially be employed, singly or in combination, provided they utilize most or all of the principal substrates present, including glucose, xylose, arabinose, glycerol, lactic acid, acetic acid, succinic acid, and cellobiose, and utilization of the non-glucose substrates in continuous culture is not unduly inhibited by the presence of glucose at 5-20 g/liter in the feed. Preferably the organisms chosen should produce yeast biomass or other valuable products in good yield on the mixed substrates. It is advantageous to produce additional yeast since it is easily recovered and can be harvested and processed in the same equipment as the fermentation yeast. *Kluyveromyces marxianus*, alone or in combination with *Candida utilis* is preferred, and benefits from supplemental niacin. Alternatively *Candida utilis* may be used by itself; it requires no vitamins but typically does not use arabinose and is not capable of growth at as high a temperature. Other suitable yeast may be identified by screening, particularly among the genera *Saccharomyces, Kluyveromyces, Pichia* and their anamorphs (asexual forms). Several strains of *Kluyveromyces marxianus* (*Saccharomyces fragilis*) are suitable including NRRL Y2415. Mixed cultures are possible where complementary substrate specificities of the two strains favor stable operation. By consuming the free sugars and fermentation by-products, including organic acids, this step enables increased water recycling within the process without the accumulation of inhibitory products. Optionally, the recycled water can be subjected to a salt-removal step (such as reverse osmosis or electrodialysis) to decrease the amount of salts returned to the process or decrease the amount of water which must be discarded to prevent salt buildup. Preferably part (20-70%) of the still bottoms is recycled directly to the starch cook and thence to the fermentation (termed "backset"), bypassing the secondary fermentation. This results in an increase in the concentration of fermentation by-products entering the secondary fermentation and permits a proportionate decrease in the size of the equipment for the secondary fermentation. Backset may also provide important nutrients to the yeast, but results in increased levels of organic acids and other solutes in the primary fermentation, which may become detrimental to performance at higher levels.

In step 108, the yeast or other biomass is harvested from the aerobic fermentation as a valuable product, leaving a stream of water from which organic acids and other inhibitory fermentation by-products have been removed. This clean water can then be recycled to the process wherever needed or optionally discharged with reduced treatment cost.

Figure 2A:
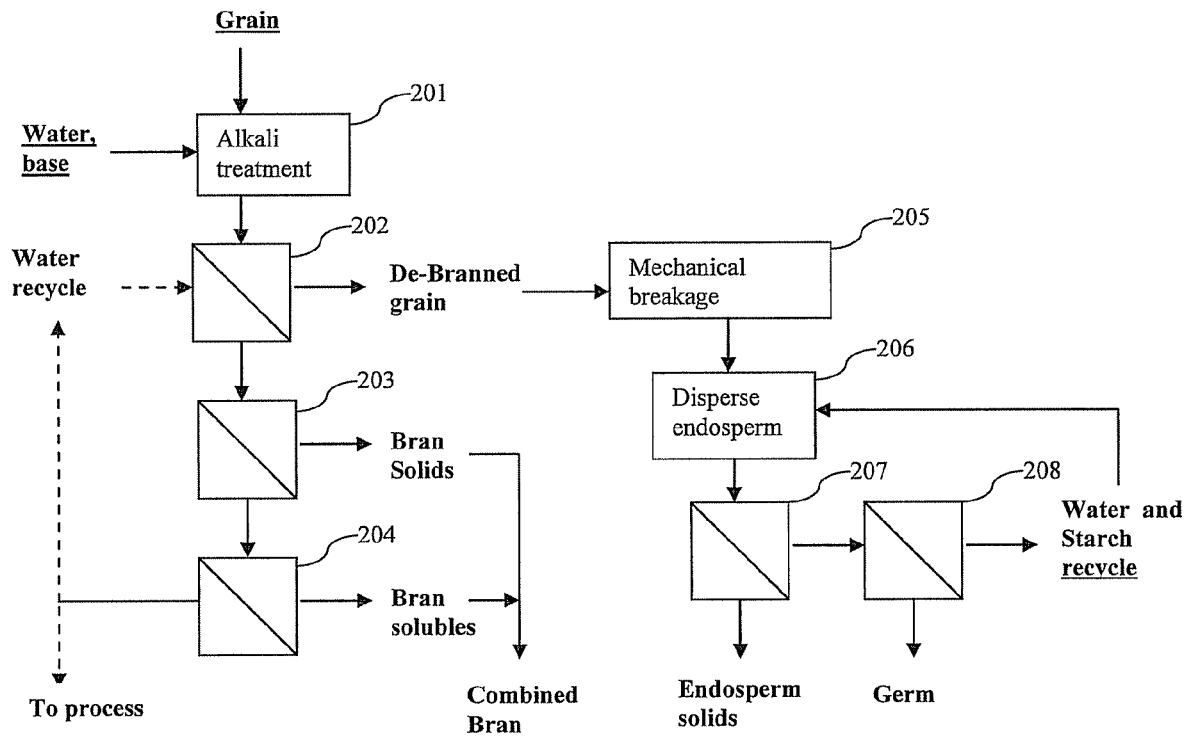
FIGS. 2A, 2B, and 2C illustrate the initial processing stage.
Figure 2B:
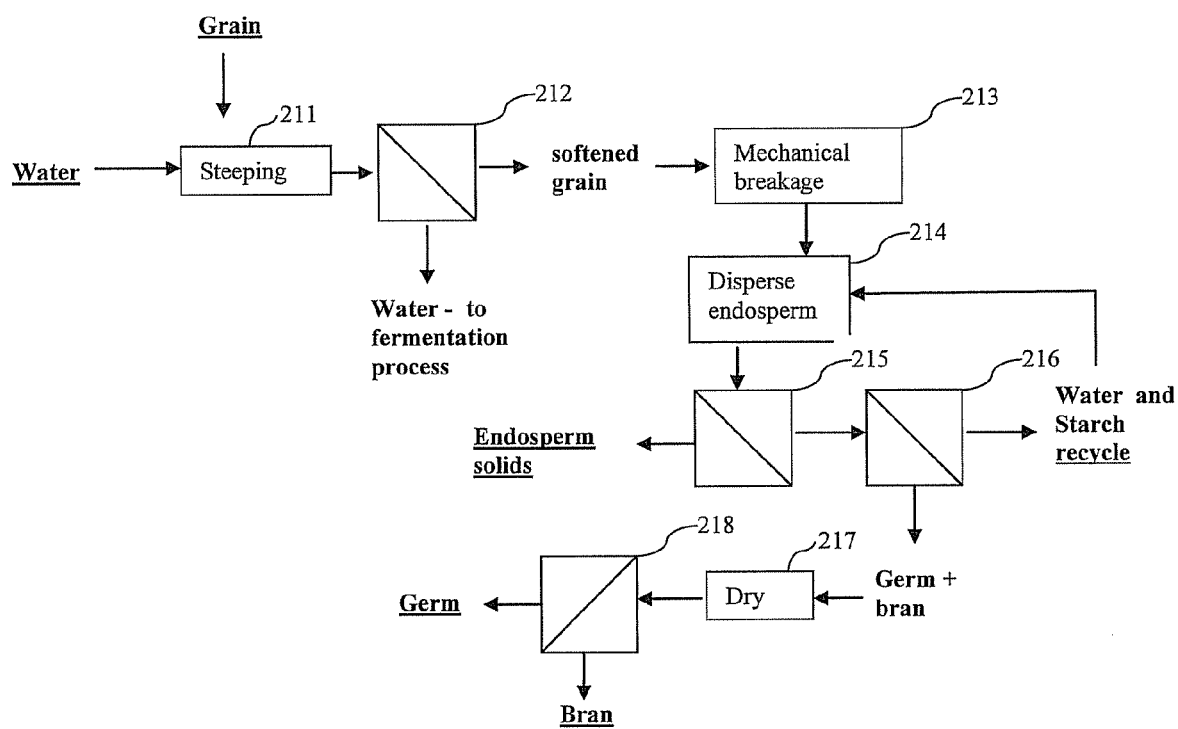
Figure 2C:
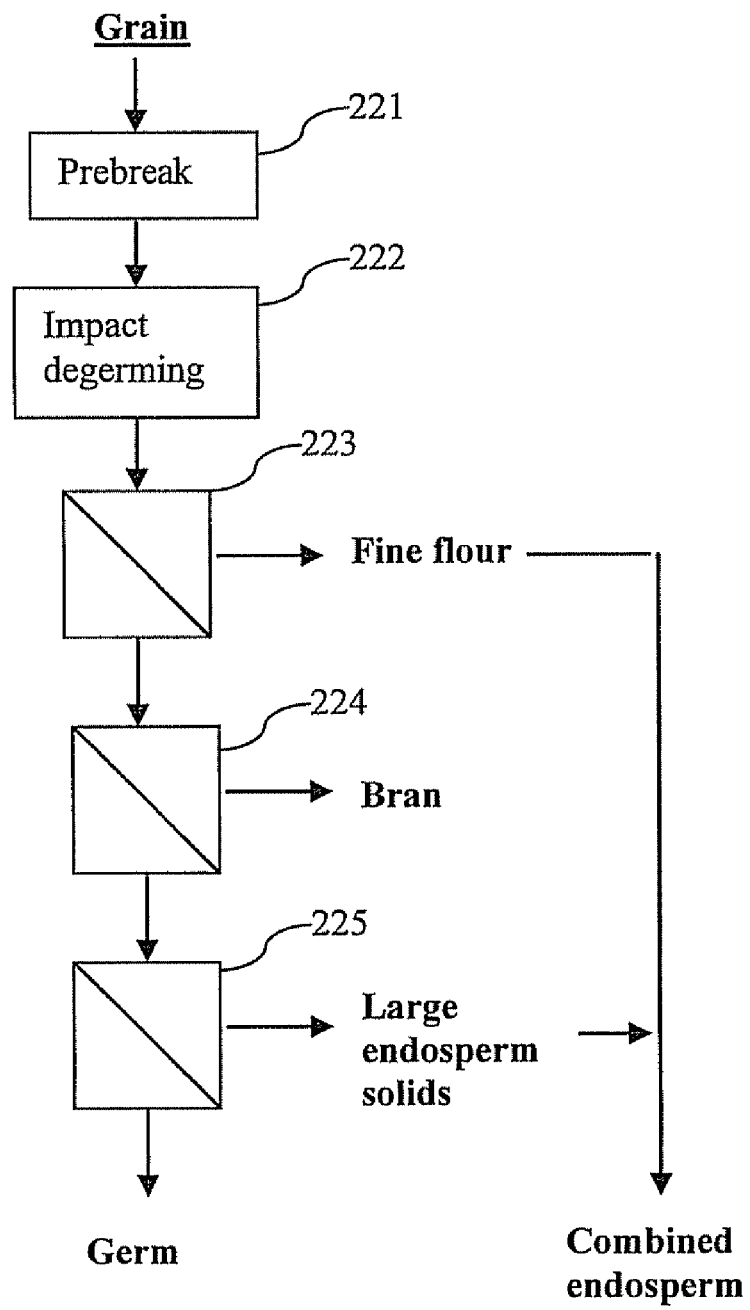

FIGS. 2A, 2B, and 2C are detailed schematics of alternate approaches to the initial processing steps of FIG. 1. The examples shown are all for corn; other grains may require modifications.

FIG. 2A illustrates initial separation employing alkaline debranning. In step 201, the grain is treated with aqueous base, preferably using the minimum amount of base possible. In step 202, the bran is washed away from the debranned grain with a spray of water on a sieve. In step 203, the bran solids are separated from the water and soluble polymers using a fine sieve and optionally dewatered using a press. In step 204, the soluble polymers and fine solids are optionally concentrated and washed by diafiltration using an ultrafilter. This fraction is then recombined with the bran solids while the ultrafiltrate is either recycled as wash water within the debran process or advanced to use as process water in downstream steps. In step 205, the debranned corn is subjected to controlled mechanical breakage using for instance an Entoleter impact mill or preferably a flaking roll mill. In step 206, the endosperm is dispersed in water with recycled endosperm starch to give a specific gravity preferably between 1.04 and 1.1 and more preferably between 1.058 and 1.072 at the process temperature. In step 207, the suspension is fractionated in a hydrocyclone of preferably 2-3 inches in internal diameter, giving a thickened suspension of starch and larger endosperm solids in the underflow, and a thinner suspension comprising mostly germ and free starch in the overflow. Finally, in step 208, the overflow and optionally the underflow (not shown) are dewatered and the germ is washed with a water spray. Water and starch are recycled to the endosperm disperser as needed and the remainder is recombined with the endosperm solids.

FIG. 2B illustrates initial separation employing short-steep wet milling and dry bran separation. In step 211, corn or milo is steeped with water to 40-45% moisture content. In step 212, the bulk of the water is separated using a sieve. In step 213, the softened grain is mechanically disrupted using, for instance, an Entoleter, a roller mill, or a Bauer mill. In step 214, the broken grain is dispersed in water at specific gravity 1.09. In step 215, the suspension is fractionated with a hydrocyclone; endosperm solids are collected at the underflow, while germ, bran, and some free starch exit in the overflow. In step 216, the germ and bran are dewatered and washed free of starch on a sieve. In step 217, the germ and bran are dried. In step 218, bran is separated from germ by aspiration.

FIG. 2C illustrates initial separation by dry milling. In steps 221 and 222, the cleaned grain is subjected to a pre-break followed by an impact step to release the germ. In step 223, the fine flour released from the soft endosperm in the initial breakage is separated on a sieve. In step 224, the bran fragments are separated from the germ and remaining large endosperm fragments by aspiration. In step 225, the germ is separated from the endosperm fragments on an air table.

Figure 3A:
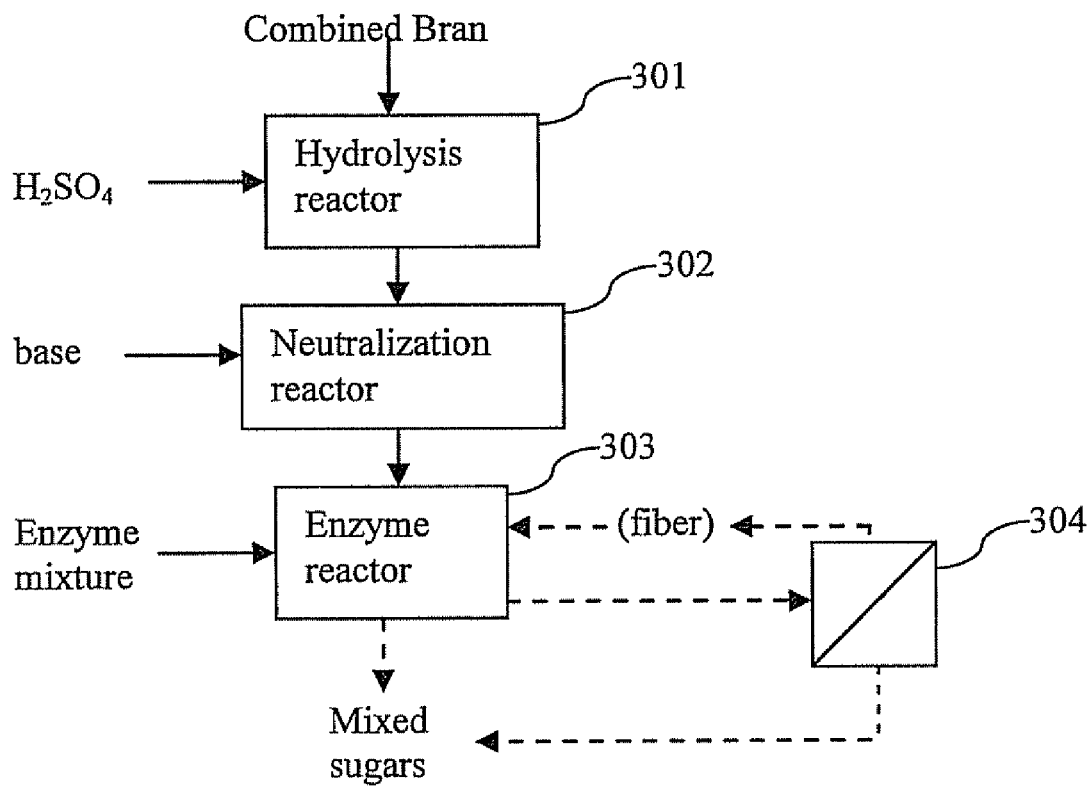
FIGS. 3A, 3B, and 3C illustrate the hydrolysis of fiber stage.
Figure 3B:
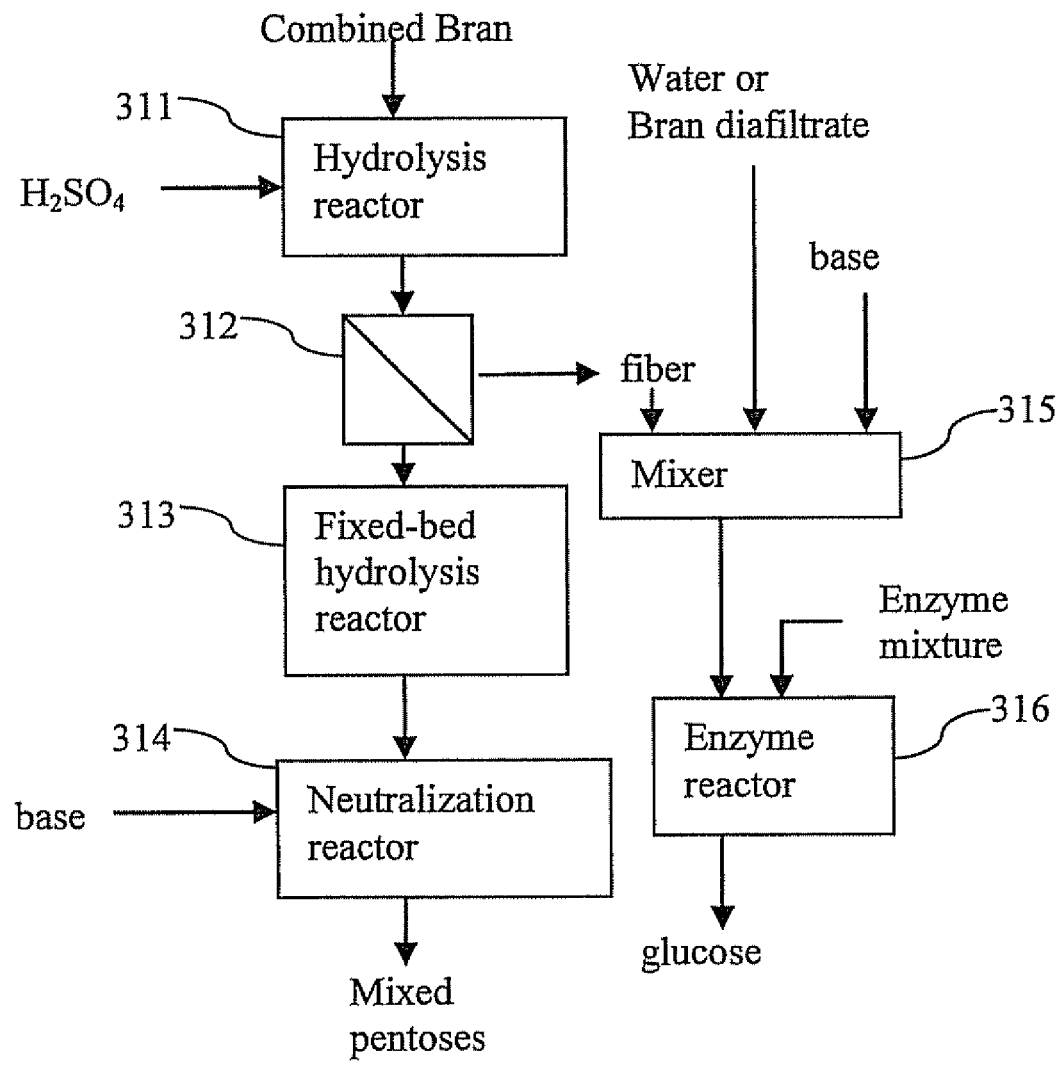
Figure 3C:
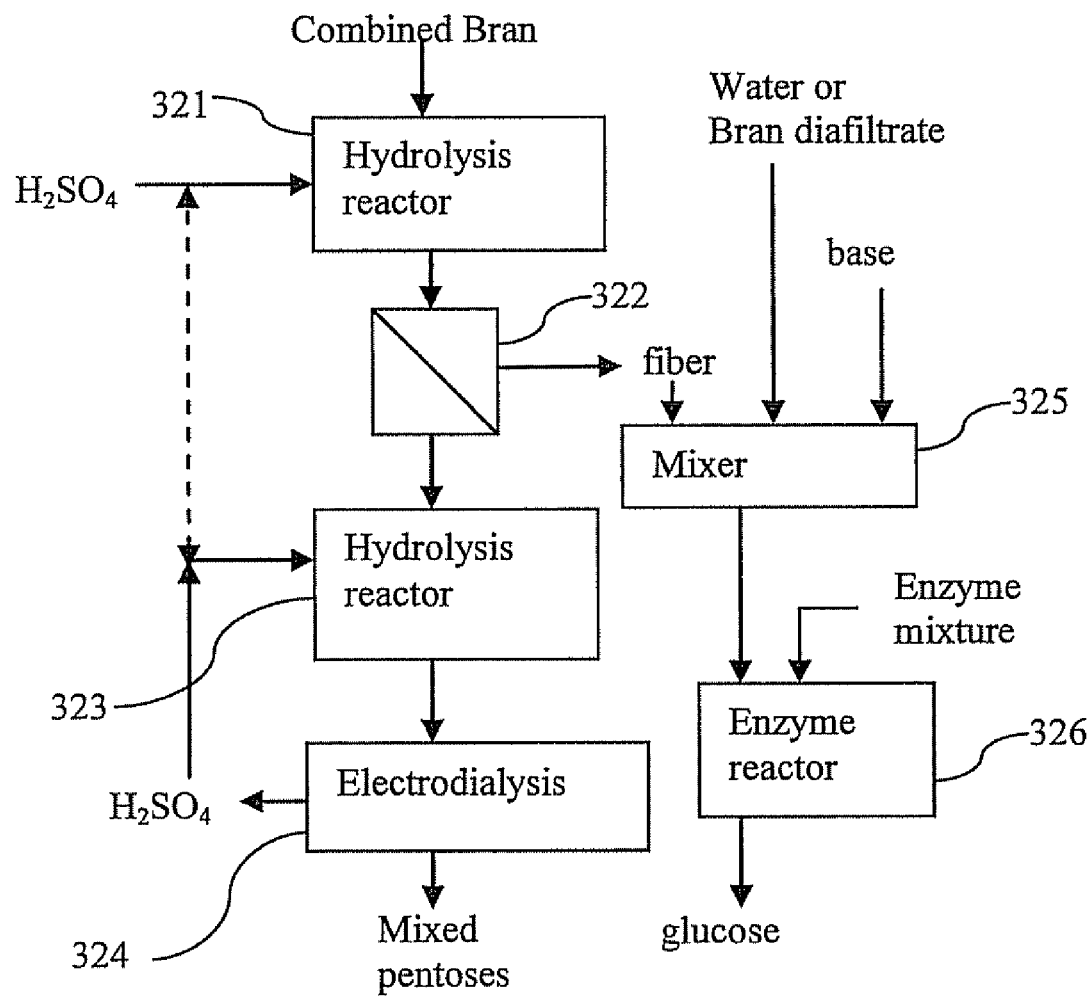

FIGS. 3A, 3B, and 3C are detailed schematic illustrations of alternate approaches to hydrolysis of fiber.

FIG. 3A illustrates sequential hydrolysis with acid and enzymes. In step 301, the combined bran stream is mixed with acid and heated under pressure, typically at pH 1.8 for 4 h at 120° C. In steps 302 and 303, the mixture is cooled and neutralized with a suitable base, then treated with a cellulase preparation, typically from *Trichoderma* sp for 24-48 hours at pH 4.5-5, 55° C. In step 304, optionally, the stream exiting the reactor is fractionated with a sieve, hydrocyclone, centrifuge, or filter to return the unhydrolyzed fiber to the reactor for further conversion.

FIG. 3B illustrates separation of cellulose fibers for separate enzyme treatment (hydrolysis of soluble pentosans using solid catalyst). In step 311, the combined bran, if necessary washed in the previous steps to reduce the salt content, is subjected to acid hydrolysis, typically at pH 2.3-3.3, 120° C. for ½ to 1 hour, preferably with vigorous mixing. In step 312, the hydrolysate is fractionated without neutralization using a sieve, centrifuge, hydrocyclone, or filter to give a fiber stream enriched in cellulose and a liquid stream containing free acid, solubilized pentosan fragments, pentoses, and other sugars released by dilute acid. For further processing in a packed bed, this stream is subjected to additional filtration if necessary to remove particulate matter >10 µm. In step 313, this stream is then passed through a bed containing a solid catalyst, such as an ion exchange resin, having immobilized strong-acid functionality. This bed may take the form of a slurry reactor, a fixed bed, or a fluidized bed, with typical residence times of 10-20 minutes at 120° C. or 1-2 h at 97° C. when using a commercial ion exchange catalyst. Suitable catalysts include CT251 and CT124, both from Purolyte Corp. Different catalysts may require different times or temperatures, which are readily determined by the artisan of ordinary skill, e.g., by experiment. In step 314, the stream exiting the reactor, predominately comprising mixed pentoses, with some free mineral acid, organic acids, and other sugars, is neutralized with a suitable base. In steps 315 and 316, the fiber stream from step 312 is re-suspended in water or the ultrafiltrate from the bran wash, neutralized with a suitable base and then treated with a cellulase enzyme preparation for 24-48 hours, giving a stream predominately comprising glucose, along with salts, some pentoses and oligosaccharides, and residual fiber components.

FIG. 3C illustrates separation of cellulose fibers for separate enzyme treatment (hydrolysis of soluble pentosans with acid recovery by electrodialysis). In step 321, the combined bran, if necessary washed in the previous steps to reduce the salt content, is subjected to acid hydrolysis, typically at pH 2.3-3.3, 100-110° C. for 1-2 hours, preferably with vigorous mixing. In step 322, the hydrolysate is fractionated without neutralization using a sieve, centrifuge, hydrocyclone, or filter to give a fiber stream enriched in cellulose and a liquid stream containing free acid, solubilized pentosan fragments, pentoses, and other sugars released by dilute acid. In step 323, the pentose-rich stream is then passed to a reactor or train of reactors for further hydrolysis at pH 1.5-2.0, 120° C., 1-4 hours residence time, with additional acid added as required. In step 324, the majority of the acid is recovered by electrodialysis or chromatgraphic methods and returned to the process at 321 and/or 323, leaving a stream containing primarily mixed pentoses with some other sugars and organic acids. In steps 325 and 326, the fiber stream from 322 is re-suspended in water or the ultrafiltrate from the bran wash, neutralized with a suitable base and then treated with a cellulase enzyme preparation for 24-48 hours, giving a stream predominately comprising glucose, along with salts, some pentoses and oligosaccharides, and residual fiber components.

Figure 4A:
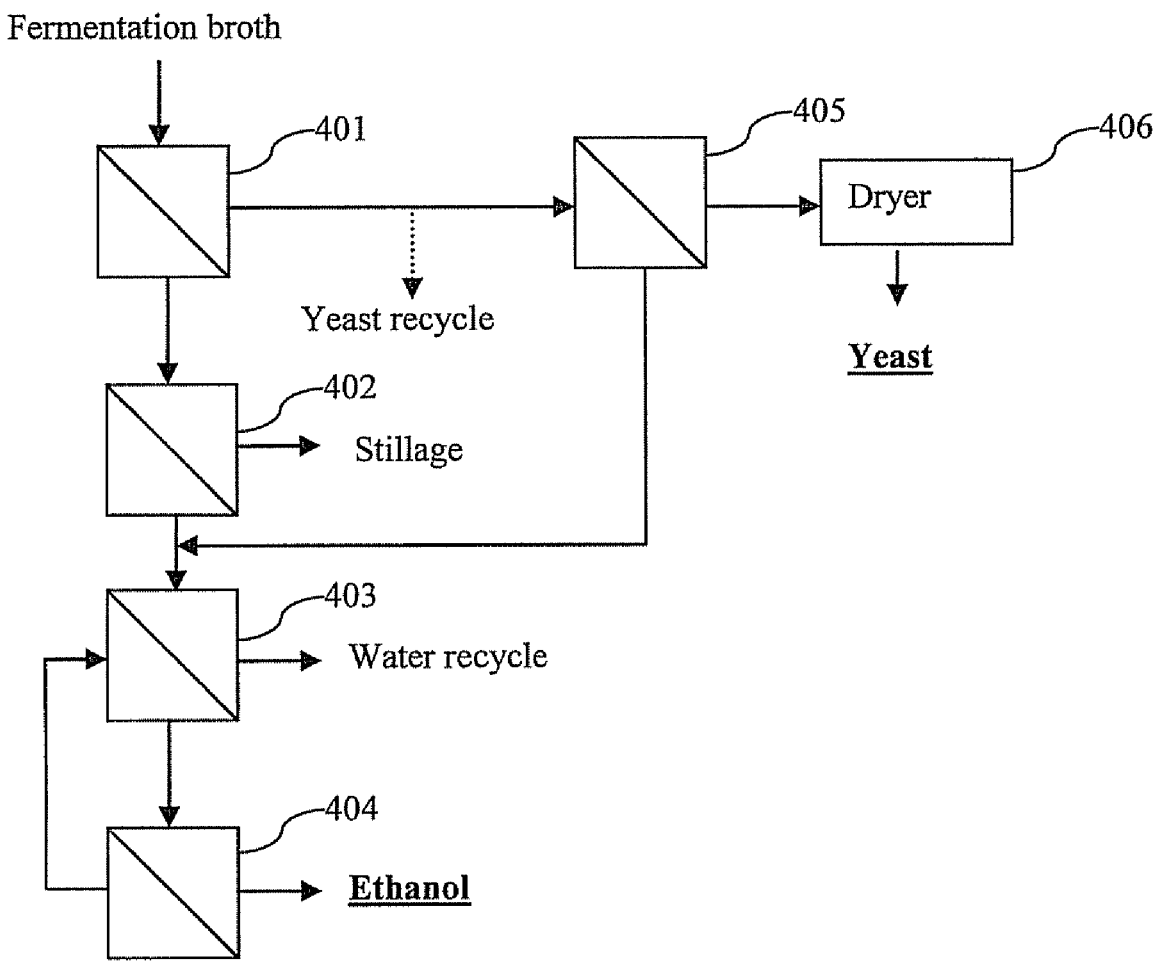
FIGS. 4A and 4B illustrate the separation of yeast, ethanol, and stillage.
Figure 4B:
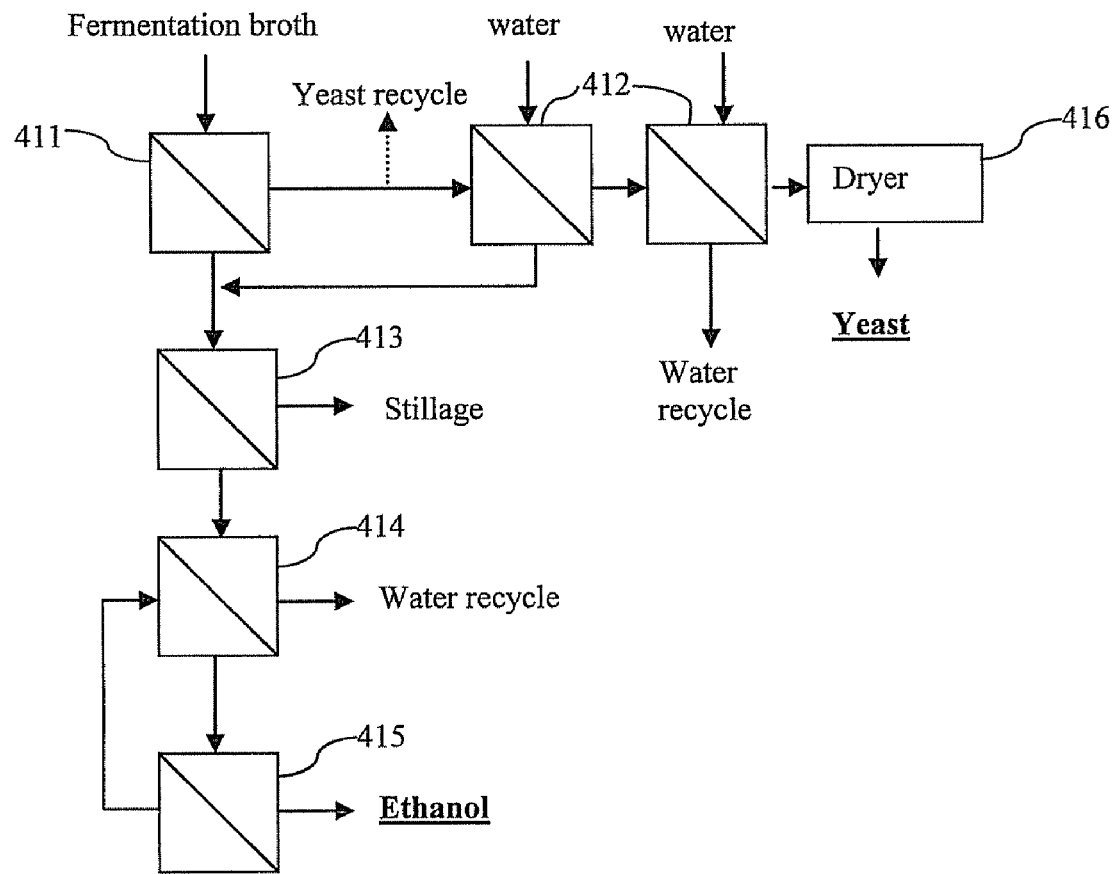

FIGS. 4A and 4B are schematic illustrations of alternate embodiments of the separation of yeast, ethanol, and stillage.

FIG. 4A illustrates distillation with pre-separation of yeast by centrifugation and separate stripper to remove ethanol from yeast.

In step 401, the fermentation broth is fractionated in a continuous disk centrifuge, decanter centrifuge, or plate thickener producing a yeast cream and a clarified broth. In step 402 the clarified broth is distilled in a stripper column. The column overhead contains water and about 50% ethanol, while the column bottoms constitute the stillage stream. This column is preferably operated under elevated pressure and temperature so that the stillage is essentially sterile. The required temperature and pressure will decrease with increasing residence time and may best be determined by the time-temperature thermal-death kinetics methods known to those skilled in the arts of biochemical engineering and food processing. In step 403, the stripper overhead is fractionated in a stripper-rectifier column or a rectifier with separate side-stripper producing 90-95% ethanol in the overhead and ethanol-depleted water in the bottoms. In step 404, the ethanol-enriched rectifier overhead is dehydrated by pressure-swing adsorption on molecular sieves or other suitable adsorbent. In step 405, the product yeast is freed of ethanol in a dedicated yeast stripper; this unit operates at lower temperature than the main stripper to preserve product quality and may be operated under vacuum at temperatures as low as 35° C. if it is desired to preserve viability or enzyme activity. The yeast stripper overhead is combined with the stripper overhead or sent directly to the rectifier. In step 406, the yeast is dried as a high-quality feed ingredient.

FIG. 4B illustrates separation of yeast by tangential-flow filtration and diafiltration. In step 411, the fermentation broth is fractionated by tangential flow membrane filtration producing a yeast cream and a clarified broth permeate. In step 412, the product yeast is freed of ethanol by diafiltration, then it is continuously mixed with a stream of water and the water and solubles are removed by tangential-flow membrane filtration. The permeate from the first diafiltration step is combined with the clarified broth prior to distillation, while the larger volume of permeate from the second step is recycled to the fermentation. In step 413, the clarified broth is distilled in a stripper column. The column overhead contains water and about 50% ethanol, while the column bottoms constitute the stillage stream. This column is preferably operated under elevated pressure so that the stillage is effectively sterilized. The required pressure to accomplish this will decrease with increased residence time, and can best be evaluated by the known time-temperature sterilization kinetics methods known to those skilled in the arts of food and biochemical engineering, taking into account any holding times at elevated temperatures. In step 414, the stripper overhead is fractionated in a stripper-rectifier column or a rectifier with separate side-stripper producing 90-95% ethanol in the overhead and ethanol-depleted water in the bottoms. In step 415, the ethanol-enriched rectifier overhead is dehydrated by pressure-swing adsorption on molecular sieves or other suitable adsorbent. In step 416, the yeast is dried as a high-quality feed ingredient.

Example 1

Enzymatic disruption of endosperm in cracked corn. Cracked corn is a commercial product, the coarsest grade of roller-milled corn. It comprises large fragments up to one-half the original kernel in size. Samples of approximately 15 g cracked corn were weighed in pared beakers, then enzyme mixtures in acetate buffer were added in volume sufficient to keep the corn immersed as it took up water. The beakers were weighed again, covered first with nylon net screens and then with foil and heated 24 h in a 50° C. bath. Periodically, the supernatant was decanted through the mesh to measure water uptake and solids release, expressed as brix of the suspension, and then returned to the beaker. After 24 hours, samples were extracted with an additional portion of water, which extracted little extra density. The solids were shaken vigorously with the combined extracts in glass jars, and the liquid phase was decanted through a nylon let screen and allowed to settle in a separate jar. The supernatant fluid was decanted and the solids were dried and weighed. The dried samples were then re-suspended in water; the sediments required dispersion in a blender. The samples were brought up to 60 ml with water and digested in an 82° C. bath, initially with 0.5 ml of a 2.5% solution of Amano bacterial alpha-amylase and 1.7 mM added $CaCl_2$. Digestion was incomplete overnight. The pH of the samples was found to be about 4.5 for the sediments and 4.8-5.2 for the screenings. The pH was adjusted to 6.5 with solid $Na_2CO_3$ and the samples were digested further with 0.5 ml additional amylase and 19 mM total added $CaCl_2$. Digestion was complete within about 10 h as judged by clear supernatants giving no blue color with $I_2$. Residual screenings (from the screenings) and sediments were dried. Sediments were brown, brittle, and often adhered tightly to the foil on which they dried; amounts were insufficient for protein analysis.

| Sample | Corn, g | Buffer, ml | Amano HC, ml | Solvay TRL, ml | Amano P, ml | total liquid, g |
|---|---|---|---|---|---|---|
| 9 | 14.75 | 5 | 5 | | | 36.29 |
| 11 | 14.8 | 5 | 5 | 10 | | 35.97 |
| 14 | 14.88 | 5 | 5 | 10 | 10 | 35.1 |
| 15 | 15.23 | 5 | | | | 37.37 |

Amano HC: 1:50 dilution of 30% w/w stock Amano Hemicellulase
Solvay TRL: 2:50 dilution of neat enzyme solution
Amano P: 2:50 dilution of 25% w/w stock Amano pectinase
Buffer: 0.83M acetate pH 4.8

| Sample | Initial brix | 24 h brix | Screenings dry wt. | Sediment dry wt. |
|---|---|---|---|---|
| 9 | 1.2 | 7.1 | 8.23 | 3.54 |
| 11 | 1.7 | 8.1 | 5.98 | 5.3 |
| 14 | 2 | 12.2 | 4.58 | 6.41 |
| 15 | 1.3 | 3.4 | 12.53 | 0.81 |

| | Extract | Residue | |
|---|---|---|---|
| Sample | brix | dry wt | protein |
| 9 scr | 5.8 | Scr2 2.37 | 20.70% |
|  |  | Sed2 0.58 | nd |
| 9 sed | 3.3 |  0.23 | nd |
| 11 scr | 3.4 | Scr2 2.36 | 18.20% |
|  |  | Sed2 0.19 | nd |
| 11 sed | 5.5 |  0.56 | nd |
| 14 scr | 14 | Scr2 2.04 | 14.70% |
|  |  | Sed2 0.01 | nd |
| 14 sed | 6.8 |  0.72 | nd |
| 15 scr | 8.3 | Scr2 4.05 | 22.80% |
|  |  | Sed2 0.89 | nd |
| 15 sed | 0.2 |  0.00 | nd | nd = not determined

Example 2

A larger-scale experiment employed approximately 210 g samples digested with 500 ul of stock Amano hemicellulase, 150 ul Multifect XL, and 150 ul Clarex ML and in 10 ml 83 mM acetate buffer pH 4.8 or 5.6 in a total of 149 ml liquid. Samples were incubated at 50° C. for 21 h total, with 30 ml additional water added at 225 min; All water was absorbed by 18 h. 200 ml additional water were added to cover and after 3 h further incubation the samples were dispersed by vigorous shaking. Samples were filtered through nylon net and the solids were re-extracted twice by further shaking with water. And rinsed a further 3×. The screenings stained only lightly for starch, with the pH 4.8 sample lighter than the 5.6 sample. The pooled sediments from the extracts and rinses, which resembled a butterscotch milkshake in color and consistency, were washed by decantation with 400 ml water. Samples of the screenings and the pooled, rinsed sediment were dried and weighed, and the remainder of each was digested with alpha amylase.

| Sample | Extract solids (refractive) | Screenings dry matter | Sediment dry matter | Total | Recovery |
|---|---|---|---|---|---|
| pH 4.8 | 31.2 | 78.2 | 97.75 | 207.15 | 107% |
| pH 5.6 | 27 | 95.5 | 81.5 | 204 | 106% |

Isolation of protein fractions from amylase digests of enzymatically dispersed corn endosperm. Sediments were adjusted to pH 6.4-6.6 with $NaHCO_3$ solid and digested with 0.5 ml amylase and 5 ml of 40 mM added $CaCl_2$ digestion at 77° C. for 3 h and 66 C overnight was incomplete. Each sample was given an additional aliquot of $CaCl_2$ and heated to 92 C briefly, then cooled to 60 C and given an additional aliquot of amylase as before. After several hours, the sediments tested negative for starch. Digested sediment samples were left to settle overnight, then decanted by siphon and similarly rinsed twice by decantation and pelleted by centrifugation.

| From sediment fractions | dry matter | Protein |
|---|---|---|
| 4.8 amylase sediment | 6.64 | 57.70% |
| 5.6 amylase sediment | 4.71 | nd | nd = not determined

Example 3

The following description of a 25 kg debranning run and its results employed a jacketed, variable-speed, single-ribbon mixer of about 3 ft³ capacity (Readco, York, Pa.). It was fitted with a stainless steel lid and o-ring seal, permitting it to be pressurized to 15 psi. The lid was fitted with a pressure gauge, rupture disk, safety valve, a thermocouple projecting into the headspace, a two inch ball valve with funnel for additions, and a ¼" ball valve for manual pressure release. A drilled-pipe spray bar was fitted through a side port and connected through an L-pattern ball valve so that it could be used to supply steam directly into the headspace or spray streams of water or base solution onto the corn as it was mixed. This spray bar could also be turned to wash down the sides of the mixer. The bottom of the mixer had a four inch ball valve to discharge product and a thermocouple port so fitted that the thermocouple could be inserted into the mass of product with the mixer stopped.

To prepare for use, the jacket was connected to a 30 psi steam source. Steam was added to the jacket to preheat the empty mixer until a jacket pressure of 18 psi was reached. Steam was also supplied through the spray bar to preheat the internal parts and headplate, for 15 minutes. Water (4.6 kg) was added to the empty, preheated mixer and heated to boiling with heat supplied through the jacket while mixing at 72 rpm. 25 kg corn was then added and mixed. When the headspace temperature reached 97° C., the pressure release valve was closed and heating was continued until the headspace temperature reached 101° C. 15 minutes after addition of the corn. At this point the corn temperature also read 101° C.

Sodium hydroxide (105 g) dissolved in 2.30 kg boiling water was transferred to a pressurizeable stainless steel dispensing tank (Alloy Products Corp.), then transferred into the mixer through the spray bar by air pressure and applied to the corn with continuous mixing. Excess air was vented through the pressure release valve. Heating was continued with the valve closed and steam addition through the spray bar so that pressure built up. Mixing and steam addition (to both headspace and jacket) were stopped 8 minutes after the sodium hydroxide was added. At this point the corn temperature was 104° C.; in other runs this temperature has reached 108° C. 9.2 kg of water at about 20° C. was then added through the spray bar with resumed mixing, the pressure release valve was opened to equalize pressures, and the mixture was agitated for 5 minutes. The product was then discharged from the mixer at about 85° C. through the bottom valve with the aid of the agitator and a further addition of 9.6 kg water through the spray bar. The product at this point was a slurry of debranned kernels in a thick brown suspension of removed pericarp.

The product slurry was transferred to a stainless steel hopper supplying a vibrating feeder (Eriez Magnetics) and applied at a steady rate to an eighteen inch SWECO gyratory screen with 6-mesh and 24 mesh sieves, such that the corn did not exceed one-half inch depth on the screen. The corn was washed on the sieve by a spray of wash water (a total of 33 kg was used) and the wash water was collected below the 24 mesh sieve and reused. A small stainless steel diverter bolted to the side next to the nozzles was employed to keep corn from bypassing the spray. The wash water was applied as a flat spray through two nozzles, angled about 15° in the direction of motion of the corn. A plexiglass lid helped contain the splatter, and a stainless steel diverter was positioned to direct the washed corn to the discharge while letting the corn which missed the spray re-circulate. Detached pericarp passed through the 6-mesh sieve and collected on the 24 mesh sieve below, from which it discharged to a separate container. It was subsequently dewatered by passing it through the apparatus again without washing. The pH of the pericarp and wash at this point are typically about 8.5.

The product debranned corn (35.5 kg) had a temperature of 53° C., moisture content 42.2%, 9.4% protein dry basis, and 2.88% neutral detergent fiber dry basis, compared with 9.2% moisture, 9.04% protein dry basis and 4.54% neutral detergent fiber dry basis in the starting corn. The wet pericarp (4.66 kg) contained a total of 265 g dry matter. The recovered wash contained 1.8% dry matter for a total of 690 g.

Adaptation for a lot of corn more difficult to debran. A lot of corn was received which had a substantial portion (about ½) rounded, reddish kernels. This lot proved difficult to debran under conditions which had worked well with other lots of corn, but could be debranned with higher base usage. For instance, in the open mixer, 4.8 g NaOH/kg corn gave partial debranning, 189.1 g wet pericarp containing 15 g dry matter from 2.5 kg corn, while 5.76 g/kg gave 455 g wet pericarp containing 32.2 g dry matter. In the pressurizable mixer, 4 g NaOH/kg corn gave no visible bran removal, 5.25 g/kg gave 5.59 kg wet pericarp containing 302 g dry matter from 23 kg corn, while 5.6 g/kg gave 5.25 kg wet pericarp containing 464 g dry matter from 23 kg corn. The rounded, initially reddish kernels were the most difficult to debran, and were darkened by the procedure.

Ultrafiltration of Pericarp Wash. The solids and colloidal material in the pericarp wash were concentrated by ultrafiltration using a Scepter tangential flow module from Graver Associates. For ten consecutive process runs, the retentate had an average dry matter content of 8.9±0.7% and represented 42±4% of the total mass and 82±4% of the dry matter. A detailed compositional analysis of the ultrafiltration permeate and retentate was performed on pilot plant prep PP5-01. On a dry matter basis the retentate contained 8.4% protein, 1.1% fat, and 68.2% polysaccharide. The composition was very similar to the pericarp fraction. The retentate accounted for 49% of the water, 89% of the dry matter, 87% of the protein, 100% of the fat, 57% of the ash, 98% of the glucan, 99% of the xylose residues, and 96% of the arabinose residues, with the permeate accounting for the remainder.

The pericarp wash ultrafiltration retentate was combined with the dewatered pericarp fraction and the combined material, referred to as combined bran, was subjected to hydrolysis procedures as described below.

Acid-enzyme Hydrolysis. Two semi-preparative hydrolysis experiments employed combined bran samples heated at low pH for heated 100, 200, 300, or 400 minutes at 120° C., then neutralized with NaOH and acetate buffer and enzyme-treated. The approximate solids content was 72.6% in the acid step and 68.1 g/l in the enzyme step. The bran used in these experiments, on complete hydrolysis, yielded 41.6% glucose, 19.8% xylose, and 8.4% arabinose on a weight/weight basis.

In the first of these time series, the bran was nominally adjusted to pH 2.0 (43 ml % M $H_2SO_4$/4800 ml combined bran, 7.5% solids). The final pH of these fractions was about 2.6. This pH shift is in part due to consumption of acid in side reactions, but is larger than usually observed, suggesting that the pH adjustment of the original bran may not have been complete.

Analysis of the washed post-acid pellets showed the enrichment of cellulase in the solid fraction during acid hydrolysis.

| pH "2.0" cook | Total glucose, xylose, and arabinose contents of washed pellets after partial acid hydrolysis | | |
|---|---|---|---|
| | glucose, % of dry matter | xylose, % of dry matter | arabinose, % of dry matter |
| Total fraction | 41.1 | 19.8 | 8.4 |
| 0 min 3x washed pellet | 50.3 | 20.1 | 8.8 |
| 400 min 3x washed pellet | 43.2 | 6.9 | 0 |

A second series was adjusted to pH 1.8 for the acid cook (84 mmol $H_2SO_4$/g solids), and then after the indicated time adjusted to pH 4.6 and digested with 3.96 mg/g solids each of Celluclast (a *Trichoderma* cellulase) and Novozyme 188 (a beta-glucosidase). This was a deliberately high enzyme loading. No xylanase was used since previous results showed that it had no effect after vigorous acid pretreatment.

| Cook time | DP3 | DP2 | Glu | Xyl | Ara | Total | Mono |
|---|---|---|---|---|---|---|---|
| Sugar contents of pre-enzyme, post-acid supernates, pH 1.8 cook, as % bran dry matter | | | | | | | |
| 0 | 0.0% | 0.0% | tr | 0.0% | 0.0% | 0.0% | 0.0% |
| 100 | 5.6% | 2.1% | 2.5% | 9.6% | 8.2% | 28.0% | 20.3% |
| 200 | 6.4% | 4.4% | 7.2% | 15.6% | 9.3% | 42.9% | 32.1% |
| 300 | 5.8% | 6.7% | 12.3% | 17.7% | 9.5% | 52.0% | 39.5% |
| 400 | 4.8% | 6.4% | 15.3% | 18.7% | 9.7% | 55.0% | 43.8% |
| Sugar contents of post-enzyme supernates, pH 1.8 cook, as % bran dry matter | | | | | | | |
| 0 | 0.0% | 1.6% | 27.7% | 1.5% | 1.0% | 31.8% | 30.2% |
| 100 | 4.3% | 2.2% | 28.3% | 14.6% | 9.9% | 59.3% | 528% |
| 200 | 4.3% | 2.4% | 29.8% | 19.5% | 11.0% | 67.0% | 60.3% |
| 300 | 3.7% | 2.9% | 31.0% | 21.4% | 11.6% | 70.6% | 64.0% |
| 400 | 3.1% | 3.1% | 30.5% | 22.1% | 11.4% | 70.2% | 64.0% |

The impact of both pH and treatment time in the acid step were investigated. In the particular experiment shown here, the pH in the acid cook was varied. The bulk material was adjusted to pH 4.7 with acetic acid prior to the experiment. Then $H_2SO_4$ was added to reach the desired cook pH and the material was autoclaved. The samples were neutralized to pH 4.6-4.7 and the remaining solids were centrifuged out (and thereby largely separated from soluble materials released in the acid step) and re-suspended in water. The samples were treated with enzymes at 55 C, pH 4.5 and sampled at 18 and 40 h. The solids, comprising mostly cellulose, were treated with a *Trichoderma* cellulase at 2 mg/g dry solids, while the soluble materials were treated with Deerland pentosanase (1.33 mg/g) and Cellulase 4000 (0.67 mg/g dry solids). Free sugars and small oligosaccharides were measured by HPLC and the residual pellets were dried and weighed. Results are expressed as g per g original dry matter.

Monosaccharide Yields. In general, the highest yield of glucose from the enzyme digestions was obtained from intermediate first-treatment pH, while the highest yield of monomeric pentoses was obtained from samples of the lowest first-treatment pH. Arabinose increased essentially linearly with decreasing pH in the acid treatment, while xylose release increased sharply at the lowest pH values (2.0>>2.3>2.6). After treatment at these low pH values there was little additional release of xylose by enzyme treatment and the enzyme treatment had little or no effect on arabinose release in any sample. Enzyme treatment did release additional xylose in samples receiving less vigorous acid pretreatment, but these never achieved the levels of the more strongly acid-treated samples.

| Mass recovery (% of starting material) | | | | | | |
|---|---|---|---|---|---|---|
| | | 41 hr digest of post-acid solids | | 41 hr digest of post-acid supernate | | |
| Cook pH | Final pellet | Total poly | Mono | Total poly | Mono | Recovery |
| 4.80 | 41.76 | 12.38 | 5.39 | 12.02 | 3.86 | 75.42 |
| 4.00 | 32.00 | 14.57 | 7.61 | 17.96 | 5.73 | 77.87 |
| 3.50 | 30.07 | 14.23 | 8.31 | 17.89 | 7.43 | 77.92 |
| 3.00 | 28.53 | 13.42 | 8.89 | 19.00 | 9.16 | 79.01 |
| 2.60 | 29.20 | 12.38 | 9.12 | 16.91 | 9.92 | 77.52 |
| 2.30 | 28.73 | 10.10 | 9.75 | 14.21 | 11.62 | 74.41 |
| 2.00 | 28.03 | 6.78 | 11.29 | 10.92 | 14.47 | 71.49 |

Substantial levels of glucose were released from the cellulose pellet by cellulase treatment, but substantial undigested solids remained; this may reflect limitation by the level of beta glucosidase in the cellulase used in this experiment. The release of glucose by enzyme treatment of the acid supernate suggests the presence of cello-oligosaccharides even after mild acid treatment. It is believed that some glucose released by enzyme treatment of the soluble fraction could have been due to hydrolysis of a small amount of contaminating starch, although it is not clear why in that case the yield would have the observed pH dependence. It is possible that some starch is native to the pericarp; starch could also be derived from broken kernals. The presence of soluble glucan or labile cellulose in the crude alkali-released bran cannot be ruled out.

| Glucose released | | | | | |
|---|---|---|---|---|---|
| Cook pH | 0 hr SN | 18 hr pellet | 18 hr SN | 41 hr pellet | 41 hr SN |
| 4.80 | 0.00 | 2.52 | 2.04 | 5.20 | 3.22 |
| 4.00 | 0.00 | 3.08 | 2.69 | 6.47 | 4.08 |
| 3.50 | 0.00 | 3.11 | 2.96 | 6.58 | 4.61 |
| 3.00 | 0.09 | 2.93 | 3.22 | 6.41 | 5.00 |
| 2.60 | 0.14 | 2.89 | 3.24 | 5.95 | 5.00 |
| 2.30 | 0.25 | 2.58 | 3.39 | 5.58 | 5.24 |
| 2.00 | 0.73 | 2.51 | 3.97 | 5.53 | 5.48 |

| Xylose released | | | | | |
|---|---|---|---|---|---|
| Cook pH | 0 hr SN | 18 hr pellet | 18 hr SN | 41 hr pellet | 41 hr SN |
| 4.80 | 0.00 | 0.00 | 0.04 | 0.00 | 0.14 |
| 4.00 | 0.15 | 0.23 | 0.31 | 0.39 | 0.39 |
| 3.50 | 0.31 | 0.35 | 0.58 | 0.57 | 0.72 |
| 3.00 | 0.55 | 0.54 | 0.97 | 0.90 | 1.19 |
| 2.60 | 0.83 | 0.84 | 1.34 | 1.29 | 1.60 |
| 2.30 | 1.39 | 1.21 | 1.99 | 1.99 | 2.40 |
| 2.00 | 3.16 | 1.95 | 3.91 | 3.24 | 4.20 |

| Arabinose released | | | | | |
|---|---|---|---|---|---|
| Cook pH | 0 hr SN | 18 hr pellet | 18 hr SN | 41 hr pellet | 41 hr SN |
| 4.80 | 0.19 | 0.15 | 0.40 | 0.19 | 0.50 |
| 4.00 | 0.94 | 0.51 | 1.17 | 0.75 | 1.26 |

-continued

| | | Arabinose released | | | |
|---|---|---|---|---|---|
| Cook pH | 0 hr SN | 18 hr pellet | 18 hr SN | 41 hr pellet | 41 hr SN |
| 3.50 | 1.76 | 0.84 | 2.08 | 1.15 | 2.10 |
| 3.00 | 2.59 | 1.09 | 2.90 | 1.59 | 2.98 |
| 2.60 | 3.14 | 1.39 | 3.30 | 1.87 | 3.32 |
| 2.30 | 3.60 | 1.60 | 3.78 | 2.18 | 3.99 |
| 2.00 | 4.37 | 1.84 | 4.77 | 2.53 | 4.80 |

The HPLC method did not resolve maltose (starch-derived DP2; DP=degree of polymerization) from cellobiose (cellulose-derived DP2). Levels of DP4+ oligomers decreased during the enzyme treatment, while DP3 glucose oligomers first increased then decreased. DP2 glucose oligomers increased with time in the digested supernates, and increased to a plateau in digests of the acid pellets. Xylo-oligomers and/or arabinoxylo-oligomers were present but not well resolved. They may contribute to the areas of the DP4+ and DP3 peaks. The final pellet represented 28-30% of the dry matter for all samples with pretreatment pH of 3.0 or below. An earlier experiment, not as thorough and across a narrower pH range, gave substantially identical trends for soluble sugars. This earlier experiment showed better release of xylose by enzyme (for pretreatment pH 2.3-4.0) than the experiment shown above, but the release was far from complete.

Perhaps the most relevant single observation is that the enzyme cocktail was ineffective in releasing free arabinose from solubilized xylan across the entire range of pH values tested for the pretreatment, even at intermediate pH values where solubilization was good and arabinose release was far from complete in the acid step.

Solid acid. Samples of partial (100-minute pH 2-2.6) hydrolysate supernate were treated at 100° C. with two different sulfonic acid ion exchangers, one gel type (Dowex 50Wx4-100) and one macroporous (Dowex MSC-1). Comparison with a control sample heated without the resin demonstrated substantial decreases in oligosaccharide peaks and commensurate increases in monosaccharide levels. In the control, 15% of the recovered sugars were monosaccharides, while in the two resin-hydrolyzed samples the monomer contents were 56 and 61%. Differences between the two resin treated samples were minimal, with the gel-type resin giving slightly higher glucose and total monosaccharide yields in this experiment.

One consideration with these catalysts is the potential for hydrolysis or elimination of the active sulfonic acid at elevated temperature. Not only does this limit catalyst life, but the free acid product can act as a catalyst, giving falsely high apparent rates of conversion. In order to check for degradation of the resin, the rate of hydrolysis of aqueous cellobiose (a beta-linked disaccharide available in high purity) by known quantities of two commercial catalyst resins, Purolyte 124 and Amberlyst 36, was measured and checked for release of titratable acidity. The results are below.

| Resin | Resin mass, g | % hydrolysis | Apparent rate constant, hr-1 | Titratable acidity, μmol/g resin | Final pH |
|---|---|---|---|---|---|
| CT124 | 0.924 | 52% | 5.2 | 24 | 3.2 |
| CT124 | 2.41 | 82% | 4.7 | 14 | 2.84 |

-continued

| Resin | Resin mass, g | % hydrolysis | Apparent rate constant, hr-1 | Titratable acidity, μmol/g resin | Final pH |
|---|---|---|---|---|---|
| Amberlyst 36 | 1.02 | 28% | 2.1 | 49 | 2.75 |
| Amberlyst 36 | 3.33 | 62% | 1.9 | 38 | 2.3 |
| Amberlyst 36 | 0.596 | 19% | 2.4 | 51 | 2.94 |

Both resins were catalytically active, and gave in each case a comparable estimate of the individual catalytic constant at different levels of catalyst, indicative of a reaction first-order in both substrate and catalyst. Although both resins released titratable acidity, the apparent catalytic activity was uninfluenced by the resulting solution pH, and the better performing catalyst actually leached less acid and had higher supernatant pH. This experiment employed as-received resins; when the same aliquots of resin were used again, less acid leached off, indicating that the acid leaching observed was probably due to unincorporated monomer rather than to desulfonation. This has subsequently been confirmed in experiments with washed resin.

Example 4

Comparison of Germ Recovery Procedures. In the "Grinding-Entoleter" procedure, the debranned corn was ground in a fourteen inch Entoleter pin mill with double-row or single-row rotor operating normally at 3000 rpm, adding the corn from a scoop smoothly rather than in slugs. In the "Grinding-Roller" procedure, the corn was applied to smooth flaking rolls (8 inch diameter, rotating at slightly greater than 60 rpm) as individual scoopfuls, not allowing buildup of corn. Roll temperature was maintained between 70 and 80 C to promote adhesion, thereby increasing throughput. The flaking roller mill was purchased at auction and was apparently originally shop-built by or for General Mills (Minneapolis, Minn., USA).

Hydrocyclone Separation—Standard Procedure. This procedure employs a Krebs two inch polypropylene cyclone with −625" vortex finder and open (0.5") tip, supplied by ¾ hp open-impeller stainless steel centrifugal pump with 1¼ inch feed and 1 inch discharge lines. For a 25 kg prep, 20 kg water is weighed water into the tank and preheated to 50° C. Ground de-branned corn is added with agitation and recirculation through the pump, taking care to achieve good dispersal to avoid clogging. Hand mixing may be necessary at first. Water is added as needed to achieve the target slurry specific gravity (1.055 for Entoleter-ground corn). The pH is adjusted to 6.0, and calcium chloride (1-2 g/kg corn) and 1 ml amylase are added to control viscosity. When the corn is well dispersed, flow is directed to the hydrocyclone with overflow and underflow recycled. pressure is typically 12-13 psi. After inspection of the streams and flow measurement, the underflow is redirected to an empty tank and the overflow to the SWECO with 26 mesh sieve. The through-screen fraction is recombined with the underflow. A second cut, if necessary, may be taken similarly.

The germ fractions are weighed before and after washing with an equal mass of water; this wash may be recombined with the through-screen and underflow fractions or analyzed separately. Subsequent washes (normally 2-3) are monitored for dry matter content and discarded in pilot plant operations; in process operations these washes would be reused in countercurrent fashion.

Modified Hydrocyclone Procedure for Roller Milled Corn. The roller mill left more large endosperm fragments than the Entoleter. This made the operation of the hydrocyclone difficult, for reasons including an increased tendency for clogging, concomitant difficulty obtaining sufficient suspension specific gravity, difficulty maintaining a uniform suspension, and interference between particles such that an appreciable percentage of large endosperm fragments were recovered in the overflow even at low (1.04) specific gravity. To remedy this, cornstarch was used as a supplemental density medium along with additional water. Results are summarized in the accompanying table. This dilution and density adjustment permitted operation at a higher specific gravity (1.065) with lower apparent viscosity and less particle-particle interference, giving the best oil content yet obtained in an initial germ cut, and further improvement from fines removal in drying (see table). In continuous industrial operation the starch would be obtained from the process and added starch would be needed only at startup.

| Comparison of first germ cuts Entoleter, standard separation | | |
|---|---|---|
| germ | washed | bulk dry |
| | fat, % dry basis | |
| 7-Nov | 28.2 | nd |
| 10-Dec | 25.5 | two preps combined |
| 18-Dec | 28.8 | 37.6 |
| Average | 27.5 | |
| SEM | 0.83 | | nd = not determined

| Roller, standard separation | | |
|---|---|---|
| germ | washed | bulk dry |
| | fat, % dry basis | |
| 14-Jan | 27.66 | 28.28 |
| 28-Jan | 31.8 | 31.5 |
| 3-Feb | 27 | 32.6 |
| Average | 28.8 | 30.8 |
| SEM | 1.23 | 1.06 |

| Roller, modified hydrocyclone separation | | |
|---|---|---|
| Germ | washed | bulk dry |
| | fat, % dry basis | |
| 18-Feb | 33 | 37.2 |

| Performance of grinding methods in releasing germ and avoiding breakage | | | | | | | |
|---|---|---|---|---|---|---|---|
| | % free intact germs | % with adherent endosperm | % ruptured kernels | % in intact kernels | % broken germs | Weight % fines | % germs in fines (visual estimate) |
| Entoleter single row high speed | 42.3% | 0.0% | 0.0% | 0.0% | 57.7% | 30.5% | 50% |
| Entoleter single row low speed | 60.5% | 8.2% | 4.3% | 2.1% | 25.0% | 10.5% | 50% |
| Entoleter single row low speed repeat | 61.1% | 9.5% | 4.0% | 0.0% | 25.4% | 11.8% | 50% |
| Entoleter double row low speed | 62.5% | 8.5% | 5.3% | 2.2% | 21.4% | 9.4% | 36% |
| roller mill .080" unheated | 49.2% | 23.7% | 17.8% | 0.0% | 9.3% | 3.7% | 50% |
| roller mill .090" unheated | 52.3% | 21.4% | 20.6% | 0.0% | 5.7% | 1.9% | 10% |
| roller mill .090" heated | 44.5% | 27.1% | 20.2% | 0.0% | 8.3% | 5.5% | 18% |
| roller mill .100" unheated | 33.0% | 20.0% | 41.7% | 4.3% | 0.9% | 2.2% | 5% |
| roller mill .110" unheated | 21.2% | 14.2% | 54.0% | 4.4% | 6.2% | 0.9% | 10% |
| roller mill .120" unheated | 21.7% | 35.0% | 29.2% | 11.7% | 2.5% | 1.2% | 5% |
| Roller mill .140" unheated | 7.3% | 3.6% | 36.4% | 50.0% | 2.7% | 0.2% | 5% |

Comparison of Roller Mill and Entoleter Results. The Entoleter pin mill was compared in three configurations. The configurations were double-row low speed, single-row low speed, and single-row high speed. The roller mill was tested with unheated rolls at gap widths from 0.080" to 0.14", in each case using alkaline-debranned corn at 50 C and 41% moisture. The roller mill was also tested with heated rolls at 0.90" gap, using the same debranned corn two days later at room temperature. The resulting ground corn was evaluated by wet screening (−10+60) and by counting germs sorted into five classes: broken germs (free or associated), free intact germs, germs with adherent endosperm, germs in ruptured kernels, and intact kernels. The (−10+60) fraction ("fines") was scored for apparent % germ (iodine-non-staining), dried, and weighed.

When only the percentage intact free germ was considered, the Entoleter operated at low speed gave the best result. However, it also gave much higher levels of broken germs and apparent germ fines. Broken germs and germ fines were minimized with the roller mill at the larger roller gap settings, but these left substantial numbers of intact and ruptured kernels. Experience indicates that most adherent endosperm and ruptured kernels are broken up in the pump or hydrocyclone, freeing the germ. Best results for combined percentage unbroken germ (free or with adherent endosperm or as part of a ruptured kernel) was obtained with a roller gap of 0.90". Operating the rolls hot at this gap dramatically improved throughput at the cost of a small increase in germ breakage and fines. Fines from the roller mill contained less germ than the comparable Entoleter fractions.

A trial with an 18" commercial roller mill gave very comparable performance at the same roll gaps. High throughput was maintained without heating the rolls, indicative of the larger rolls gripping the kernels more effectively due to the smaller effective nip angle.

Example 5

Production of Protein Fractions. Corn was debranned by the usual alkaline process producing bran and wash fractions, and the debranned corn was ground, dispersed in water, and fractionated with a hydrocyclone to produce germ and endosperm cuts. The endosperm suspension was adjusted to pH 6.0 at 50° C., and calcium chloride (52 g per 30 kg original corn) was added, along with alpha-amylase (Termamyl, 15 ml per 30 kg original corn). Heat was provided by a steam coil discharging condensate at atmospheric pressure. In the standard starch cook procedure the slurry was heated with vigorous stirring and recirculation to 60 C at 1 C/minute, then to 78 C at 0.5 C/minute, then to 85 C at 1 C/minute. After 1 hour at 85 C, the slurry was heated to 95 C at 1 C/minute and held a minimum of 50 minutes or until a negative iodine test was obtained. At this point, the slurry was covered and allowed to cool slowly overnight with continued stirring.

| Yield of PFC and Hydrolysate | | | | | |
|---|---|---|---|---|---|
| Fraction | Moisture | Wet mass, kg | Dry matter, kg | Protein, kg | Fat, kg |
| Starting material | 75.4% | 83.3 | 20.47 | 1.64 | .48 |
| PFC >710 μm | 83.6% | 5.7 | .93 | .22 | .038 |
| PFC <710 μm | 91.9% | 18.6 | 1.51 | .53 | .031 |
| Hydrolysate <120 μm | | 53.4 | | — | .41 |

93% recovery of wet mass

The slurry was reheated to 50 C before fractionating by sieving. The solids were collected as two size cuts, with the demarcation diameter approximately 710 μm (25 mesh). The finer fraction was collected on a 120 mesh (125 μm) sieve. These solids, designated PFC, were dried after washing once on the sieve or else held for further processing. In three similar runs, the through-screen fraction was further fractionated by ultrafiltration on a Graver membrane filter (1.5 sq ft area), once with diafiltration to lower the residual dextrin content. In two similar runs starting from the same batch of debranned corn, the cooking was done in a steam-jet cooker, adding the enzyme in two parts, before and after steam cooking. One of these runs preheated the corn to 85° C., the other to 65° C.

Appearance and Bulk Properties of PFC. Wet PFC is a finely-divided resilient creamy yellowish solid. When it is dewatered by pressing or filtration it readily takes up water again. It dries with an open texture and a noticeably fibrous appearance at small scale. Unwashed PFC browns to a variable degree on drying at 103° C. Under the microscope it is seen to comprise free fiber, aleurone fragments with their characteristic thick cell walls and protein-staining interior, and fragments of endosperm protein. The endosperm protein takes the form of spongy "starch ghosts" retaining the imprint of the starch granules removed earlier in the process. This matrix is largely disrupted by digestion with a Bacillus protease. Similar structure is readily recognizable, but less pronounced, in material processed by jet cooking. Many of the protein fragments show remnants of the endosperm cell walls appearing as flat prisms perpendicular to the line of sight or else as lines edge-on. These show the presence of residual carbohydrate when stained by the periodic acid-Schiff reagent method (PAS). There is no evidence of starch remaining in this complex, but some small globules of retrograde starch are visible in aggregates of fine debris separate from the protein fragments. Most of the free fiber stains intensely with PAS but some fine cellulose fibers are present which stain only weakly but show intense birefringence. Some of the PAS-positive fibers have streaks or spots of protein visible on their surface when counterstained with fast green. PFC prepared by jet cooking appears to be somewhat larger and more heterogeneous in size than material prepared by atmospheric pressure batch cooking.

| PFC Fractionation and Enrichment of Protein | | | | | | |
|---|---|---|---|---|---|---|
| | % | | | | | |
| | protein | fat | glucan | Arabinoxylan | ara/xyl | ax/protein |
| PFC - 26 + 120 fraction | 26.2 | 2.67 | 51.2 | 6.3 | 0.49 | 0.24 |
| amylase (hot) | 62.4 | nd | 11.5 | 10.0 | 0.77 | 0.16 |
| amylase (hot), glucoamylase | 64 | nd | 11.36 | 12.3 | 0.69 | 0.19 |
| control - hot soak, filtered, rinsed | 65.1 | nd | 8.43 | 10.3 | 0.78 | 0.16 |
| control - filtered and rinsed only | 60.1 | nd | 9.94 | 10.2 | 0.74 | 0.17 |
| hemicellulase | 66.7 | nd | 10.61 | 7.2 | 0.75 | 0.11 |
| glucoamylase | 63.7 | nd | 9.7 | 10.0 | 0.75 | 0.16 | nd = not determined

The starting PFC is seen to be enriched in glucan. Since microscopy shows only traces of cellulosic fiber in this fraction, this glucan is presumably dextrin along with some retrograde starch. Samples of PFC slurry were heated in a boiling water bath for 2 hours with or without alpha-amylase at pH 5.7. One amylase-treated sample was cooled and adjusted to pH 4.7 and treated further with glucoamylase, 105 min at 55° C. while the other two samples were filtered hot. Two additional pH 4.7 samples were incubated in parallel with glucoamylase alone or with hemicellulase, in each case for 4 h at 55° C. These samples were filtered directly. A sixth sample (control) was filtered without other treatment. All filtered samples were rinsed with an equal volume of tap water. All the treated samples were depleted in glucan and enriched in protein and arabinoxylan relative to the starting PFC, consistent with most of the glucan being soluble dextrin entrained in the porous protein matrix. Arabinoxylan was not enriched to so great an extent as protein, suggesting some was soluble. Only the hemicellulase-treated sample showed a further decrease in the arabinoxylan/protein ratio relative to the controls. When the PFC was diluted in water and fractionated in a 1" hydrocyclone, and the overflow and underflow solids were concentrated and washed by filtration, both fractions were depleted in glucan similarly to the samples in the experiment just described. The overflow was relatively more enriched in protein, while arabinoxylan was more enriched in the underflow.

Ultrafiltration. In three runs, the screened hydrolysate was further fractionated by ultrafiltration with a Graver $TiO_2$-stainless steel composite membrane. This membrane concentrated both protein and oligosaccharide material from the hydrolysate. The permeate contained about 19% refractive dissolved solids for a without diafiltration, while the retentate contained 30.7% total solids. For a run with diafiltration (diafiltration water about equal to feed) the permeate contained 13% dissolved solids while the retentate contained 7.9%. A centrifuged sample of the retentate contained 3.3% supernatant refractive dissolved solids. The diafiltration run retained higher transmembrane flowrates as the concentration factor increased. On a dry-matter basis the retentate without diafiltration contained 11.6% protein and 2.37% fat. The diafiltered sample contained 36.2% protein and 9.36% fat. The increase in protein content reflects better removal of carbohydrate material during diafiltration.

Sedimentation. The fine protein fraction can also be recovered separately for soluble polymeric material by centrifugation or gravity sedimentation. This was routinely accomplished in a benchtop centrifuge at 1000 times gravity for ten minutes to estimate solids and prepare supernates for refractometry. These solids also settled out of fermentation broths in 10-22 h at one times gravity.

Example 6

Pilot-Scale Ethanol Fermentation of Endosperm Hydrolysate and Pericarp Hydrolysate For this experiment, corn endosperm amylase digests from which the coarse protein fraction had been removed were stored frozen, then thawed overnight before use. Endosperm hydrolysate totaling 111.8 kg was combined with 18.75 kg of a cellulase digest of acid-treated combined bran. 12.1 kg of the overall mixture was removed before addition of enzymes and urea, leaving 118.5 kg mash.

Fermentation was conducted in a shop-built covered stainless-steel fermenter using a pump-around loop for agitation. The fermenter was sanitized with hypochlorate and rinsed with water before use.

Two 750 ml batches of yeast were prepared to inoculate the fermenter. The inoculum was grown in a modified YPD medium prepared in 1 liter stir flasks and stored in a water batch at 92° F. for 2 hours with air sparging. Cell count when used was $297 \times 10^6$ cells/ml with 97% viable.

| Media for Inoculations 2–750 ml batches per pilot fermenter batch Modified YPD Medium | |
|---|---|
| Glucose | 10.0 g |
| Yeast Extract | 5.0 g |
| Peptone | 10.0 g |
| Yeast | 10.0 g |

The following were added to start the fermentation.

| | | |
|---|---|---|
| Glucoamylase | Genencor Distillase L400 | 31.2 ml |
| Protease | Genencor GC 106 | 1.0 ml |
| Penicillin | Alltech ALLPEN | 0.034 g |
| Lactrol | Alltech Altoside 247 | 0.023 g |
| Yeast inoculum | Alltech Thermosac Yeast | 1.5 l |
| Urea | | 59.7 g |

After one hour, two 300 ml samples were removed from each baby fermenter and transferred into two 500 ml stir flasks for the laboratory anaerobic fermentations. Aliquots (2 ml) of corn oil were added to defoam the lab fermentations. The fermentations were monitored periodically for $CO_2$ weight loss from the flasks and HPLC analysis was run on the finished material.

The temperature of the pilot fermenter was maintained between 31 and 33° C. by heating or cooling as necessary. The pH held within the range 3.89-4.19 without adjustment. Cell count at 22 h was $383 \times 10^6$ cells/ml with 100% viable by methylene blue staining.

Samples were removed periodically from the fermenter for HPLC testing to determine ethanol and sugar content.

temperature for each strain as determined in previous tests. Three different inoculum growth states were included to test for catabolite repression.

The medium (Medium 1) used to grow the starter cultures contained 0.5 g/l corn steep powder, 0.5 g/l yeast extract, 0.25 g/l monopotassium phosphate, 0.25 g/l magnesium sulfate heptahydrate, 0.3 g/l Urea and 1.0 g/l D-xylose or 1.0 g/l glucose adjusted to final pH 4.4.

The cultivation medium contained 0.5 g corn steep powder; 0.5 g yeast extract; 0.25 g/l monopotassium phosphate; 0.25 g magnesium sulfate heptahydrate; 0.3 g/l urea; 0.125 g/l D-glucose when present, 0.125 g/l D-xylose when glucose

| Time, h | DP3+ % | DP2 % | Glucose % | Succinic acid % | Lactic acid % | Glycerol % | Ethanol % |
|---|---|---|---|---|---|---|---|
| 10 | 4.79 | 7.30 | 4.12 | 0.02 | 0.28 | 0.49 | 2.24 |
| 22 | 3.21 | 0.92 | 0.25 | 0.05 | 0.29 | 0.7 | 6.71 |
| 51 | 0.62 | 0.23 | 0.03 | 0.07 | 0.29 | 0.77 | 9.22 |

Xylose and arabinose from the pericarp hydrolysate were identifiable in the chromatograms but were not quantified.

At the end of fermentation the beer was cooled to 20° C. and let settle for 21 hours. The yeast and protein solids (36 kg slurry) were removed by decanting, and the beer (65.7 kg) was removed, weighed and transferred to the stripper tank. Steam was sparged into the stripper for two hours. The ethanol content was monitored. After the ethanol (0.356% after stripping) was removed, stillage was collected and stored cold in buckets pending transfer to frozen storage.

Example 7

Growth of Strains of *Candida utilis* and *Kluyveromyces marxianus* in Mixed Carbon Medium with and without Glucose The purpose of this test was to determine growth curves for *Candida utilis*, NRRL Y900 and *Kluyveromyces marxianus*, NRRL Y2415 in a complex medium containing mixed carbon sources including the typical fiber sugars xylose, arabinose, and cellobiose, along with the anaerobic fermentation by-products acetic acid, lactic acid, and glycerol. Cultures were grown with and without the presence of glucose at the best was not present, or 0.250 g./l D-xylose when glucose was not present; 0.125 g/l D-cellobiose; 0.125 g/l L-arabinose; 0.125 g/l (D,L)-lactic acid; 0.125 g/l glycerol; 0.0625 g/l sodium succinate; and 0.0625 g/l acetic acid adjusted to final pH 4.4.

*Candida utilis* and *Kluyveromyces marxianus* were grown overnight (18 hr) in 120 ml of starter medium with glucose in 500 ml flasks. *Candida utilis* was grown at 35° C./200 rpm and *Kluyveromyces marxianus* was grown at 40° C./200 rpm. These overnight cultures (10 ml) were used to inoculate each strain into 100 ml of starter medium with glucose and starter medium with xylose. The subcultures (exponential phase inosula) and the overnight cultures (stationary phase) were incubated an additional four hours at the respective temperatures. These flasks were used to inoculate (25 ml) duplicate samples of 250 ml of cultivation medium, and cultivation medium with glucose. Densities of all cultures were determined at 0, 2, 4, 6, 8, 10 and 24 hours using a Klett-Summerson Photoelectic Colorimeter. Ten (10) milliliters of each sample were centrifuged at 5,000 rpm for 10 minutes; supernatants were decanted and stored at −20° C. for subsequent HPLC analysis. The results are summarized in the following tables.

| | | | | | | | | | |
|---|---|---|---|---|---|---|---|---|---|
| Results of Growth Curve Analyses on *C. utilis*, NRRL Y900 and *K. marxianus*, NRRL Y2415. | | | | | | | | | |
| Yeast | Starter Conditions major sugar | Glucose added | Cell Density in Klett units | | | | | | |
| | | | 0 hr. | 2 hr. | 4 hr. | 6 hr. | 8 hr. | 10 hr. | 24 hr. |
| *C. utilis* | Exponential glucose | Yes | 29 | 62 | 108 | 140 | 161 | 170 | 181 |
| *C. utilis* | Exponential glucose | No | 30 | 56 | 108 | 141 | 162 | 162 | 178 |
| *C. utilis* | Stationary glucose | Yes | 30 | 49 | 104 | 140 | 161 | 159 | 173 |
| *C. utilis* | Stationary glucose | No | 30 | 49 | 100 | 141 | 161 | 163 | 176 |
| *C. utilis* | Exponential xylose | Yes | 30 | 29 | 50 | 116 | 147 | 166 | 173 |
| *C. utilis* | Exponential xylose | No | 30 | 30 | 48 | 117 | 148 | 164 | 181 |

-continued

Results of Growth Curve Analyses on
C. utilis, NRRL Y900 and K. marxianus, NRRL Y2415.

| Yeast | Starter Conditions major sugar | Glucose added | \multicolumn{7}{c}{Cell Density in Klett units} | | | | | | |
|---|---|---|---|---|---|---|---|---|---|
| | | | 0 hr. | 2 hr. | 4 hr. | 6 hr. | 8 hr. | 10 hr. | 24 hr. |
| K. marxianus | Exponential glucose | Yes | 20 | 76 | 118 | 132 | 150 | 168 | 185 |
| K. marxianus | Exponential glucose | No | 21 | 68 | 118 | 135 | 133 | 157 | 169 |
| K. marxianus | Stationary glucose | Yes | 21 | 59 | 120 | 138 | 147 | 159 | 169 |
| K. marxianus | Stationary glucose | No | 21 | 62 | 105 | 139 | 147 | 170 | 177 |
| K. marxianus | Exponential xylose | Yes | 12 | 45 | 95 | 140 | 147 | 170 | 173 |
| K. marxianus | Exponential xylose | No | 12 | 32 | 83 | 144 | 151 | 175 | 188 |

Residual Substrate at 24 Hours-C. utilis.
Grams Solute per Liter for Three Inoculum Conditions

| Medium | Exponential glucose | Stationary glucose | Exponential xylose |
|---|---|---|---|
| Lactic acid | 0.125 | 0.000 | 0.000 | 0.000 |
| Acetic acid | 0.0625 | 0.000 | 0.000 | 0.000 |
| Succinic acid | 0.0625 | 0.000 | 0.000 | 0.000 |
| Cellobiose | 0.125 | 0.000 | 0.000 | 0.000 |
| Xylose | 0.125 | 0.000 | 0.000 | 0.000 |
| Arabinose | 0.125 | 0.108 | 0.109 | 0.109 |
| Glycerol | 0.125 | 0.000 | 0.000 | 0.000 |
| Glucose | 0.125 | 0.000 | 0.000 | 0.000 |
| Lactic acid | 0.125 | 0.000 | 0.000 | 0.000 |
| Acetic acid | 0.0625 | 0.000 | 0.000 | 0.000 |
| Succinic acid | 0.0625 | 0.000 | 0.000 | 0.000 |
| Cellobiose | 0.125 | 0.000 | 0.000 | 0.000 |
| Xylose | 0.25 | 0.000 | 0.000 | 0.000 |
| Arabinose | 0.125 | 0.153 | 0.076 | 0.097 |
| Glycerol | 0.125 | 0.000 | 0.000 | 0.007 |
| Glucose | 0 | | | |

Residual Substrate at 24 Hours - K. marxianus.
Grams Solute per Liter for Three Inoculum Conditions

| Medium | Exponential glucose | Stationary glucose | Exponential xylose |
|---|---|---|---|
| Lactic acid | 0.125 | 0.000 | 0.000 | 0.000 |
| Acetic acid | 0.0625 | 0.000 | 0.000 | 0.000 |
| Succinic acid | 0.0625 | 0.000 | 0.000 | 0.000 |
| Cellobiose | 0.125 | 0.028 | 0.024 | 0.015 |
| Xylose | 0.125 | 0.000 | 0.000 | 0.000 |
| Arabinose | 0.125 | 0.020 | 0.020 | 0.013 |
| Glycerol | 0.125 | 0.090 | 0.104 | 0.059 |
| Glucose | 0.125 | 0.000 | 0.000 | 0.000 |
| Lactic acid | 0.125 | 0.000 | 0.000 | 0.000 |
| Acetic acid | 0.0625 | 0.000 | 0.000 | 0.000 |
| Succinic acid | 0.0625 | 0.000 | 0.000 | 0.000 |
| Cellobiose | 0.125 | 0.038 | 0.021 | 0.020 |
| Xylose | 0.25 | 0.000 | 0.000 | 0.000 |
| Arabinose | 0.125 | 0.000 | 0.000 | 0.000 |
| Glycerol | 0.125 | 0.091 | 0.004 | 0.000 |
| Glucose | 0 | | | |

Although the pattern of substrate use showed clear evidence of catabolite repression by glucose, and also to a lesser extent by xylose with K. marxianus, overall good utilization of the substrates was achieved. C. utilis was apparently incapable of using arabinose, and K. marxianus was slow to use glycerol, especially when grown in the presence of glucose.

Example 8

Continuous Aerobic Fermentation

Test Method. Continuous fermentations studies were conducted in a New Brunswick Multigen Fermentor with a 500 ml flask. The flask was fitted with three baffles, an agitator with two flat-blade turbines powered by a magnetic drive with speed control, a filtered and metered air source at 1 L/min distributed at the base of the agitator, an aseptic sampling device, a dissolved oxygen probe (disabled for these experiments) and temperature control using a submerged heater. Sterilized medium was delivered to the fermentation by a Watson-Marlow peristaltic pump range from 0.1 to 8.0 ml/min). No pH control was employed.

Typically the test conditions for these experiments were:

| | |
|---|---|
| Agitator speed | 400 rpm |
| Fermentation temperature | 34° C. |
| Airflow | 1.0 l/m |
| Medium feed rate | 0.1-1.0 ml/min |
| Fermentor volume | 350-400 ml |

The medium formula was 4 g/l glucose, 4 g/l xylose, 2 g/l arabinose, 4 g/l glycerol 4 g/l monopotassium phosphate, 6 g/l ammonium sulfate, 0.2 g/l magnesium sulfate, 1.5 g/l yeast extract, and 3.0 mg/l niacin (when used). The carbohydrates and the salts were sterilized in separate containers and mixed together with 1000× niacin (1 ml/l) when used.

Results. Results appear in the tables below.

Fermentation Run No. 1

| Day | Residence Time (hrs) | pH | % Glucose Utilization | % Xylose Utilization | % Arabinose Utilization | % Glycerol Utilization |
|---|---|---|---|---|---|---|
| 1 | 12.3 | 3.5 | 100 | 89 | 84 | 85 |
| 2 | 12.3 | 3.3 | 100 | 52 | 47 | 33 |

-continued

Fermentation Run No. 1

| Day | Residence Time (hrs) | pH | % Glucose Utilization | % Xylose Utilization | % Arabinose Utilization | % Glycerol Utilization |
|---|---|---|---|---|---|---|
| 3 | 12.3 | 2.7 | 100 | 92 | 84 | 5 |
| 4 | 7.7 | 2.8 | 100 | 90 | 92 | 20 |
| 5 | 5.1 | 2.3 | 100 | 85 | 75 | 15 |
| 6 | 5.1 | 2.7 | 100 | 94 | 90 | 40 |
| 7 | 5.1 | 3.0 | 100 | 78 | 66 | 22 |
| 8 | 4.4 | 2.7 | 100 | 68 | 50 | 16 |
| 9 | 7.7 | 2.9 | 100 | 52 | 42 | 13 |
| 10 | 12.3 | 2.9 | 100 | 78 | 76 | 17 |
| 11 | 7.7 | 2.9 | 100 | 88 | 80 | 20 |

Substrate use-up is shown above. Utilization of glucose was complete for all conditions. Utilization of xylose and arabinose varied between 50 and 90%. Glycerol utilization was generally 15-20%. The initial medium pH was 4.9. The fermentation pH fell to 2.5-3.1 without pH control. The fermentation was not $O_2$-limiting as evidenced by the lack of ethanol formation during fermentation. The limiting growth rate was greater than 0.228/hr since there was no washout.

Fermentation Run No. 2

| Day | Residence Time (hrs) | pH | % Glucose Utilization | % Xylose Utilization | % Arabinose Utilization | % Glycerol Utilization | Wet Cell Wt. |
|---|---|---|---|---|---|---|---|
| 1 | 7.0 | 3.1 | 100 | 17 | 10 | 6 | 17.0 |
| 2 | 7.0 | 2.8 | 100 | 84 | 80 | 10 | 18 |
| 3 | 7.0 | 4.3 | 100 | 69 | 58 | 16 | 31 |
| 4* | 7.0 | 4.9 | 100 | 95 | 93 | 97 | 36 |
| 5* | 7.0 | 6.4 | 100 | 75 | 85 | 100 | 48 |
| 6* | 7.0 | 6.3 | 100 | 100 | 98 | 100 | 59 |
| 7* | 5.2 | 4.3 | 100 | 100 | 95 | 100 | 60 |
| 8* | 5.2 | 3.8 | 100 | 96 | 89 | 100 | 44 |

*Medium change to 50% pericarp hydrolysate and 50% initial medium + 2X niacin addition.

Substrate utilization is shown above. As expected, all of the glucose was utilized. Utilizations of xylose and of arabinose were each greater than 85%. Glycerol utilization was low at the start of the run but improved after the change of medium and the addition of extra niacin. The pH shifted up to 4.5-6.4. The fermentation was not $O_2$-limiting as evidenced by the lack of ethanol formation during fermentation.

Example 9

Continuous aerobic fermentation with pH control. A further series of aerobic fermentations were carried out with *Kluyveromyces marxianus*. The New Brunswick Scientific MultiGen™ fermenter with a working volume of approximately 500 mL was again operated as a continuous fermenter, with the addition of automatic pH control. The vessel and medium reservoir were set up and sterilized prior to fermentations. The medium reservoir bottle was filled with sterile medium in a laminar flow hood. The pH probe was cleaned with hypochlorite and 95% ethanol and inserted into the reactor after the vessel had been sterilized and mounted on its drive base. Medium was pumped into the fermenter to the full working volume, and aeration and agitation were started. Automatic pH control was started later, at various times in different runs, using sterile acid or base added by a peristaltic pump.

The inoculum culture was prepared as follows. 100 mL of YPX broth (10 g/L yeast extract, 20 g/L bacteriological peptone, and 20 g/L xylose) was sterilized in a 250 mL baffled Erlenmeyer flask. When the broth cooled to room temperature it was inoculated with 200-250 µL or a colony of stock *K marxianus* culture. The inoculum was then incubated to reach high cell density and used promptly. The amount of inoculum used was calculated to give an initial cell density of $5 \times 10^6$ cells/mL in the fermenter.

The fermenter was maintained under the following baseline conditions. Temperature was generally 30-33° C. Agitation was set at 600 RPM, and aeration was set at 1 L/min. Under baseline conditions, the pH controller was set to maintain a pH of 4.60 for run AF 10 and 5.55 for run AF 15. The range of residence times for the reactor in these experiments was 18 to 42 hours. Corn oil (in both experiments) or Ivanhoe Industries Antifoam XFO-5502 (in run AF 15) was added as needed to control foam.

Samples were collected as needed using the sampling port. Cell numbers were measured in two ways. A spectrophotometer was used to measure optical density, and this number was used to calculate cell density using a calibration curve prepared using data from multiple experiments with the *Kluyveromyces marxianus* starting strain. Direct cell counts were also performed periodically. Dry cell weight was used to calculate yeast yield daily during the fermentations. Due to foam fractionation, the dry cell weight measured from the reactor sample is somewhat higher than that measured from overflow collection. The yeast yields shown are those taken directly from the reactor. HPLC was used to measure the carbohydrates and acids present at regular intervals to monitor the level of substrate consumption.

Run AF 10. The medium consisted of the following ingredients: 8 g/L glucose (when present), 4 g/L xylose, 2 g/L arabinose, 8 g/L glycerol, 2 g/L lactic acid, 0.4 g/L succinic acid, 0.4 g/L acetic acid, 1.6 g/L yeast extract, 4 g/L potassium phosphate monobasic, 2 g/L $MgSO_4 \cdot 7H_2O$, and 6 g/L ammonium sulfate. The salts were autoclaved separately from the carbohydrates, acids, and yeast extract. After autoclaving, 1 mL/L each of trace mineral premix solutions #1 and #2, and 500 µL/L niacinamide (4 g/L) were added. Trace mineral solution #1 contained 90 g/L $CaCl_2 \cdot 2H_2O$ and 520 g/L $MgCl_2 \cdot 6H_2O$. Trace mineral solution #2 contained 2.48 g/L $FeSO_4 \cdot 7H_2O$, 3.80 g/L $MnSO_4 \cdot H_2O$, 0.5 g/L $CuSO_4 \cdot 5H_2O$, $2.3 \times 10^{-3}$ g/L $ZnSO_4 \cdot 7H_2O$, $2.3 \times 10^{-3}$ g/L $CoSO_4 \cdot 7H_2O$, $3.3 \times 10^{-3}$ g/L $Na_2MoO_4 \cdot 2H_2O$, $7.3 \times 10^{-3}$ g/L $H_3BO_3$, $1.7 \times 10^{-3}$ g/L KI, and $2.5 \times 10^{-3}$ g/L $NiSO_4 \cdot 6H_2O$.

A previous experiment had shown that growing the inoculum culture with xylose as its only carbon source improved the rate of glycerol utilization. The first batch of medium used in this run also had no glucose to test whether its absence would improve the utilization of glycerol. Automatic pH control with sterile 1M NaOH was started prior to inoculation so that conditions in the fermenter would be favorable.

This run showed rapid onset of glycerol utilization compared with previous runs with glucose present at the start. At 24 hours the level of glycerol was 0.14 g/L, however sufficient cell density to sustain the high level of substrate consumption was not immediately obtained. The yeast level actually decreased for the first four days. Starting approximately on day 4 to day 14, the yeast concentration steadily increased from 0.5 g/L to 14.5 g/L, and in this time complete utilization of glycerol was achieved. Once dry cell weights in the fermenter reached 6 g/L or higher, all medium components were maintained below 1 g/L, even with higher medium flow rates. The fermenter maintained a steady state of yeast yield and substrate utilization until day 17. During this time the media flow rate was increased from 0.20 mL/min to 0.46 mL/min. At the lower flow rate, glycerol was completely consumed. With the increased flow rate less than 1 g/L glycerol was not being consumed, but was not building up over this time period. Towards the end of fermentation process stillage was added as half of the medium. Unfortunately, pH control had failed just previous to this, and the cells were already stressed. Even so consumption of process substrates was progressing well, with glycerol and most other components less than 1 g/L. This fermentation was terminated because of time constraints. As long as pH, foam, and other conditions such as aeration were maintained, the utilization of medium components was good.

Run AF 15. A similar fermentation was performed using thin stillage from two large-scale anaerobic fermentations as the medium. These fermentations approximately followed example 6, but employed a 90 liter ERMA fermenter, and the endosperm hydrolysate was fractionated by ultrafiltration on a 1.5 ft² Scepter tangential flow ultrafiltration module (Graver Associates) to remove fine protein fragments. In the first anaerobic fermentation, endosperm hydrolysate permeate alone was used as substrate. In the second, endosperm hydrolysate permeate was mixed with combined bran hydrolysate in rough proportion to what was produced in the process. At completion of anaerobic fermentation the yeast (or yeast and bran) was separated using the Scepter ultrafiltration module, and ethanol was distilled from the remaining permeate to produce thin stillage. Prior to use as aerobic medium, the stillage was analyzed for free sugars and acids and additional xylose and arabinose were added to make 8 g/L xylose and 4 g/L arabinose. Yeast extract, minerals, and niacinamide were also added in the same concentrations as above to ensure good yeast growth. The inoculum used was a *K. marxianus* variant that arose in a previous continuous fermentation. It had a more filamentous phenotype and utilized glycerol slightly more quickly in shake flask experiments than the wild type.

In this fermentation, automatic pH control with sterile 1M $H_2SO_4$ was started on day 14. The pH of the thin stillage without adjustment was about 5.8. Once pH control was started at 4.6, it became clear that the culture performed better at a higher pH of 5.55. When foam was not controlled it negatively affected substrate utilization. Antifoam agent (Ivanhoe Industries) controlled the foam much better than corn oil. When running at the preferred pH with foam well controlled, most substrate components were maintained below 2 g/L with good yeast yield. The only components that were not reduced in concentration were apparent glucose oligomers DP2, DP3, and DP4+.

Under favorable conditions in these two experiments *K. marxianus* was able to consume all carbohydrates and acids present in the ideal medium, and consume the same species from process stillage. *K. marxianus* was able to maintain high cell density and substrate utilization with residence times as low as 18 hours. The yeast yield was approximately 10-14 g/L for AF 10, and approximately 15-18 g/L for AF 15. As mentioned previously, the yeast yield from overflow is lower by a few percentage points due to foam fractionation. Glycerol was the last medium component to be fully consumed, and the most sensitive to changes in fermentation conditions such as pH. However when cell density was adequate, pH control was stable, and foam was controlled, glycerol was greatly reduced. An unknown analyte appeared in AF 6 at low levels, and was present in all subsequent fermentations. Through HPLC comparison it was found to be arabitol. The amount present was typically between 0.1 and 0.5 g/L.

On the basis of these results, we believe it is possible to operate a plant producing, from each bushel of cleaned #2 yellow corn of 14.5% moisture content and normal protein content, at least 2.8 gallons undenatured ethanol; at least 4.5 lb of a protein product containing at least 60% dry basis crude protein (Nx6.25) and no more than 11% moisture; and at least 2.6 lb yeast (combined *Saccharomyces* primary yeast and *Kluyveromyces* secondary yeast) having a crude protein content of at least 45% dry basis and no more than 11% moisture. We further believe that this can be accomplished simultaneously with production of a germ product of at least 33% hexane-extractable crude fat content (dry basis). Furthermore, we believe that with careful attention to detail including adequate supply of ammonia, ammonium salts, or urea as nitrogen source, at least 2.85 gallons of undenatured ethanol per bushel can be produced simultaneously with at least 4.3 lb/bu combined yeast as described above, and the protein and germ products listed above. We believe that some further improvement over the levels quoted is achievable using standard process improvement methods within the skill of the art once in the possession of the disclosure above.

Thus, variations on the invention schematically illustrated and described above are within the level of skill in the art.

We claim:

1. A method for processing corn into ethanol, comprising:
   (a) separating the corn into a bran, a germ, and a starch-and-protein mixture;
   (b) hydrolyzing the bran into a bran hydrolysate comprising free sugars;
   (c) hydrolyzing the starch in the starch-and-protein mixture of step (a) into a hydrolyzed mixture comprising a starch hydrolysate and protein which is insoluble in the starch hydrolysate;
   (d) separating the protein from the hydrolyzed mixture of step (c);
   (e) anaerobically fermenting yeast and the starch hydrolysate to produce an anaerobic fermentate;
   (f) separating the anaerobic fermentate of step (e) into (i) a first anaerobically fermented yeast stream, (ii) the ethanol, and (iii) a mixture comprising water and fermentation by-products;
   (g) aerobically fermenting yeast and the mixture comprising water and fermentation by-products of step (f) to consume at least part of the fermentation by-products, wherein the aerobically fermented yeast is the same or different than the yeast of step (e); and
   h) separating the result of step (g) into a second stream of the aerobically fermented yeast of step (g) and water.

2. The method of claim 1, in which step (e) further comprises anaerobically fermenting a portion of the bran hydrolysate of step (b) and a portion of the starch hydrolysate of step (c).

3. The method of claim 1, in which the aerobically fermenting of step (g) further comprises adding a portion of the free sugars from step (b) to the mixture comprising water and the fermentation by-products prior to the fermenting of step (g).

4. The method of claim 1, in which the separating of the corn of step (a) comprises removing pericarp from the corn.

5. The method of claim 1, in which step (a) further comprises applying controlled impact to corn.

6. The method of claim 1, in which step (a) further comprises rolling the corn.

7. The method of claim 1, in which step (a) further comprises isolating the germ from the starch-and-protein mixture by flotation.

8. The method of claim 1, in which the starch in the starch-and-protein mixture comprises an endosperm starch and is hydrolyzed with amylase in step (c).

9. The method of claim 1, in which the free sugars of step (b) comprise at least one sugar selected from the group consisting of a pentose and a hexose.

10. The method of claim 1 in which the protein which is insoluble in the starch hydrolysate is isolated from the mixture of step (c) after step (e).

11. The method of claim 1, further comprising treating the insoluble protein of step (d) to reduce the soluble fiber content thereof.

12. The method of claim 1, further comprising treating the insoluble protein of step (d) to reduce the colloidal fiber content thereof.

13. The method of claim 1, further comprising drying the removed insoluble protein obtained from step (d).

14. The method of claim 1, in which an aerobic fermentation fraction of step (f) comprises at least one of an unfermentable sugar, a glycerol, and an organic acid.

15. The method of claim 1, in which the aerobically fermenting of step (g) further comprises producing a second stream containing the aerobically fermented yeast.

16. The method of claim 1, further comprising fermenting the free sugars from the starch hydrolysate into ethanol.

17. The method of claim 1, further comprising forming a pentose from the bran hydrolysate.

18. The method of claim 1, further comprising forming a hexose from the bran hydrolysate.

19. The method of claim 1, further comprising recovering the water from step (h) for recycling in the method.

20. The method of claim 1, in which any yeast therein is selected from the group consisting of *Saccharomyces cerevisiae, Candida utilis, Kluyveromyces marxianus*, a member of the genus *Pichia*, and combinations thereof.

21. The method of claim 1, in which any yeast therein is selected from the group consisting of *Candida utilis* NRRL Y900, *Kluyveromyces marxianus* NRRL Y2145, and combinations thereof.

* * * * *